United States Patent [19]
Fosslien

[11] 4,120,662
[45] Oct. 17, 1978

[54] SPECIMEN SAMPLING APPARATUS
[75] Inventor: Egil Fosslien, Tampa, Fla.
[73] Assignee: Cortex Research Corporation, Tampa, Fla.
[21] Appl. No.: 870,453
[22] Filed: Jan. 18, 1978
[51] Int. Cl.² ............................................ G01N 1/14
[52] U.S. Cl. .................................... 73/425.6; 422/63; 422/100
[58] Field of Search ..................... 23/259, 253 R, 292, 23/230 R; 73/425.4 R, 425.6

[56] References Cited

U.S. PATENT DOCUMENTS

| | | | |
|---|---|---|---|
| 502,754 | 8/1893 | Peacock | 194/63 |
| 2,528,945 | 11/1950 | Carpenter | 89/1.5 H |
| 3,418,080 | 12/1968 | Rochte et al. | 23/259 |
| 3,431,886 | 3/1969 | McCormick et al. | 118/10 |
| 3,511,356 | 5/1970 | Bilocq | 198/29 |
| 3,554,702 | 1/1971 | Shanbrom et al. | 23/259 |
| 3,607,097 | 9/1971 | Auphan et al. | 23/259 |
| 3,653,540 | 4/1972 | Offutt | 221/75 |
| 3,768,526 | 10/1973 | Sanz et al. | 23/253 R |
| 3,832,140 | 8/1974 | Lorch et al. | 23/259 |
| 3,883,306 | 5/1975 | Widen | 23/253 R |
| 3,918,913 | 11/1975 | Stevenson et al. | 23/259 |

Primary Examiner—R.E. Serwin
Attorney, Agent, or Firm—Koenig, Senniger, Powers and Leavitt

[57] ABSTRACT

Apparatus for obtaining samples from specimens of blood or the like contained in a series of closed containers, which specimens include a plurality of particles such as cells. A pair of parallel feed screws moves the closed containers along a predetermined path to a sampling station and in one mode, a mixing mode, imparts motion to the closed containers while they are moved along the path to obtain a substantially uniform distribution of the particles contained therein. The apparatus includes a needle which penetrates the closed containers when they reach the sampling station to withdraw specimen samples from the containers. The apparatus includes a controller for tilting each closed container at the sampling station so that one end of the container is lower than the other end. The needle penetrates the lower end of the container.

53 Claims, 25 Drawing Figures

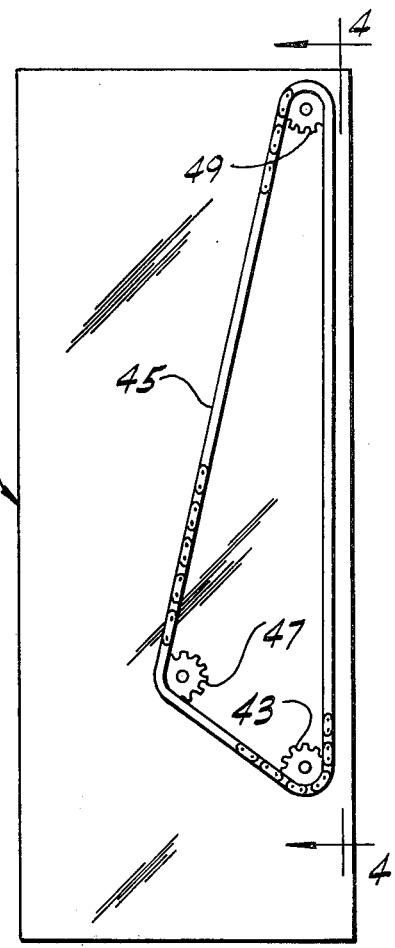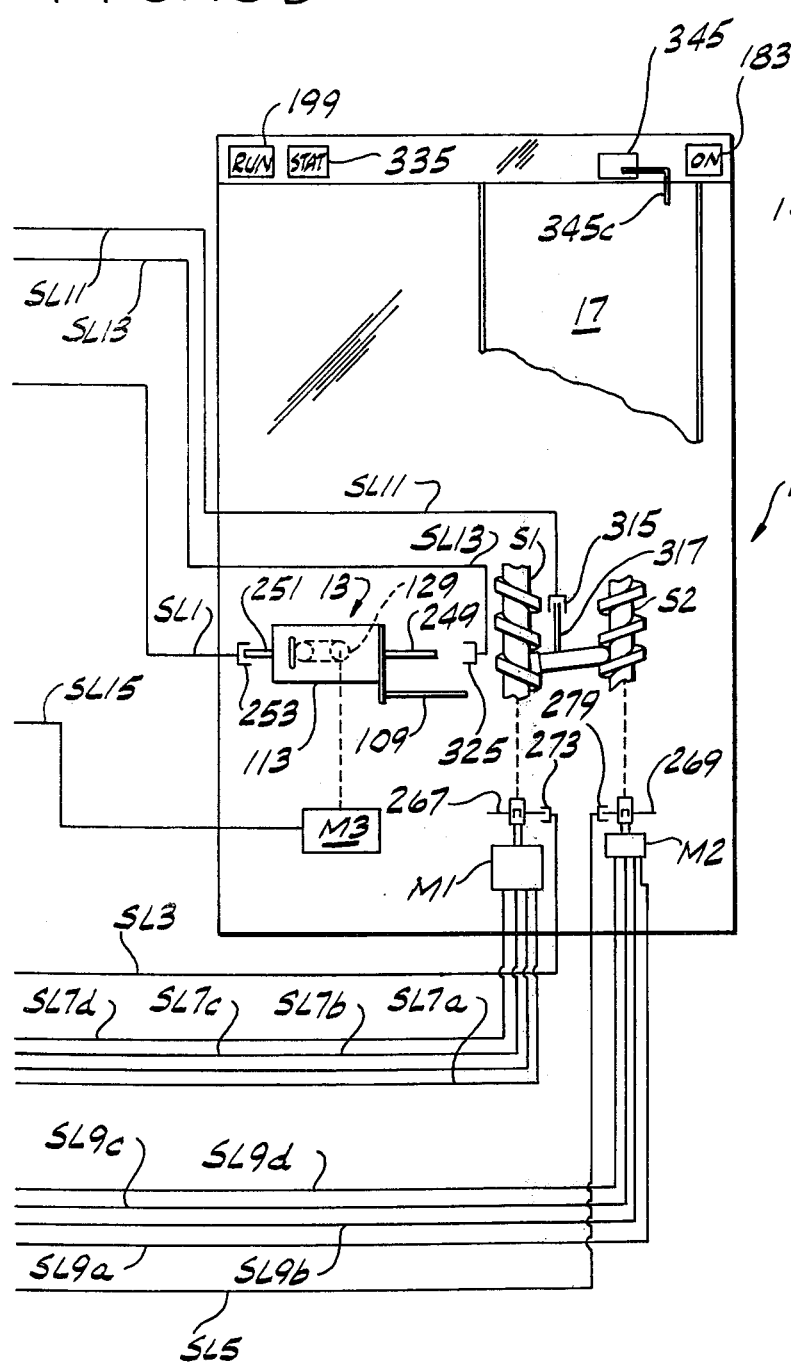

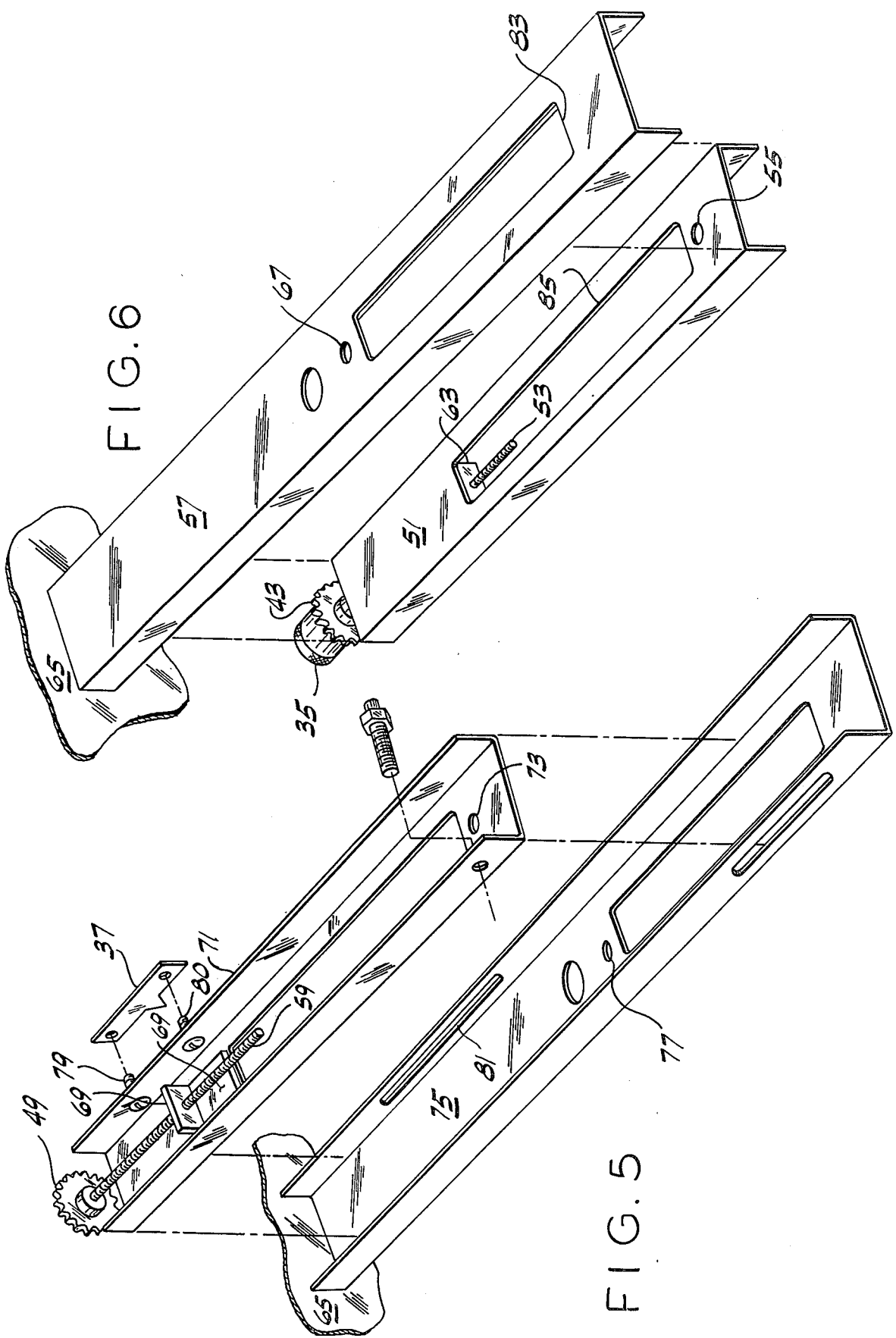

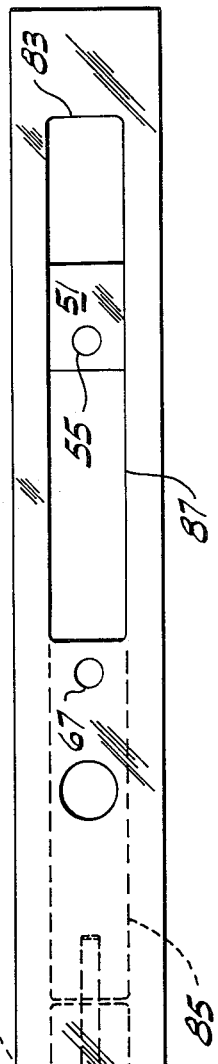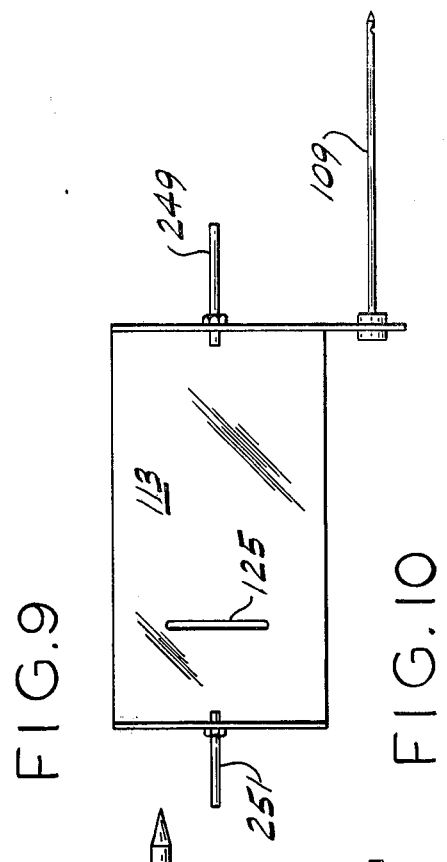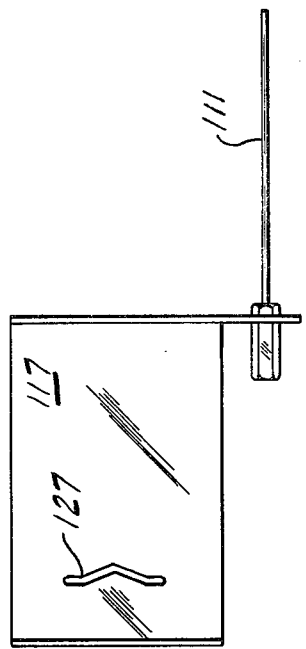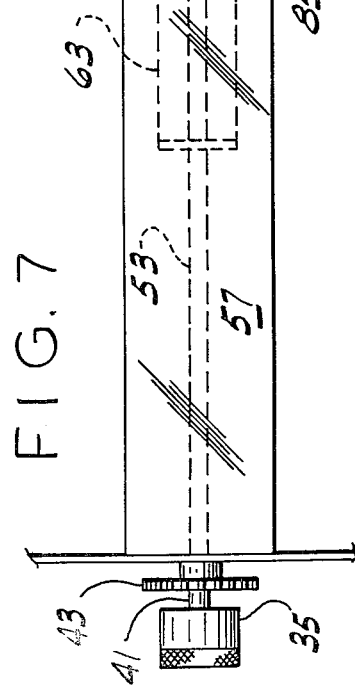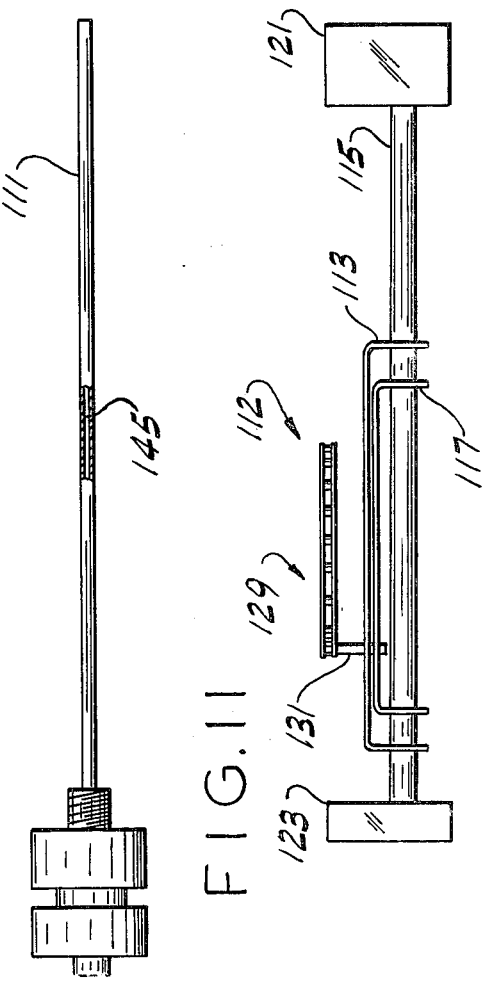

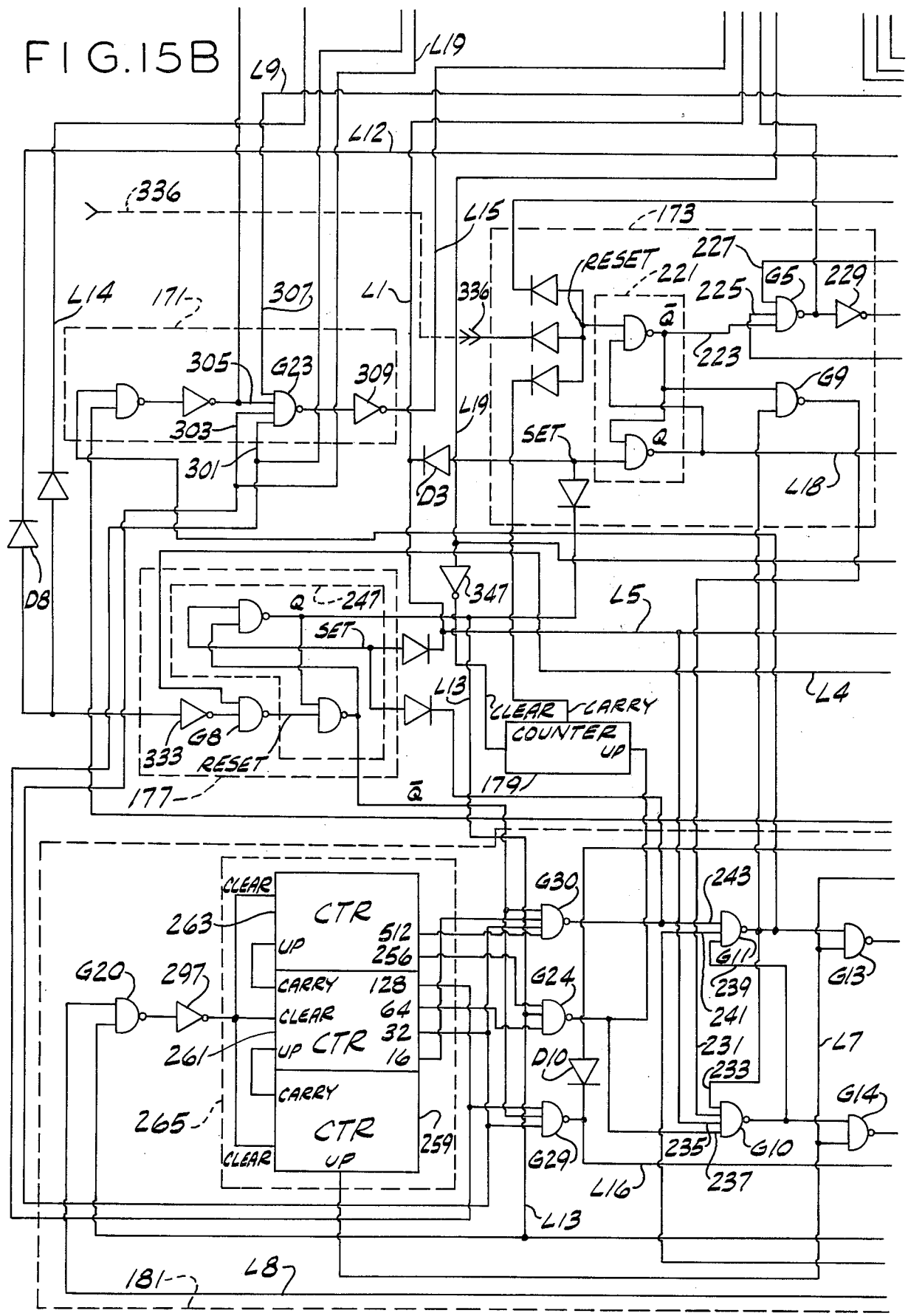

SPECIMEN SAMPLING APPARATUS

BACKGROUND OF THE INVENTION

This invention relates to laboratory sampling apparatus and more particularly to apparatus for obtaining samples from specimens of blood or the like contained in a series of closed containers.

Such apparatus are typically used in hospitals or commercial medical laboratories in performing various tests on specimens of whole blood or blood serum. Whole blood specimens are drawn from the patient and kept in glass tubes with rubber stoppers, such as those sold under the trade designation "Vacutainer" by Becton, Dickinson and Company of East Rutherford, New Jersey. In many cases the glass tubes also contain an anticoagulant. Before the blood in these tubes is analyzed, it is gently and carefully mixed to obtain an even distribution of blood cells. After mixing, a sample of each specimen is taken and subsequently analyzed as desired, e.g., analyzed for cell count or classification.

Sampling of blood serum is similar, except for the mixing step. A specimen of blood serum is typically obtained by separating it from whole blood in a serum separator tube such as those sold under the trade designation "Corvac" by the Corning Glass Works of Corning, New York. In these tubes a thixotropic gel barrier is formed between the blood serum and the other constituents of the whole blood specimen. Because of the presence of this thixotropic gel, it is not desirable to agitate such tubes. Blood serum specimens are, therefore, sampled and analyzed, but not mixed.

Current apparatus, however, are not without disadvantages. Apparatus which provide only a sampling function usually sequentially sample specimens placed in a linear or circular tray. In most of these, movement of the specimen tubes takes place in a generally horizontal plane, thereby taking up much valuable bench space. When blood serum is being sampled, these samplers require the use of some system for sensing the level of the liquid in the specimen tube. When whole blood is being sampled, these samplers must be used in conjunction with a mixer, a separate piece of equipment. The drawbacks of using two separate pieces of equipment, a mixer and a sampler, are readily apparent. The specimen tubes must be physically transferred from the mixer to the sampler, which wastes time and manpower. There is also the possibility that during this operation a specimen tube will be broken, lost or rendered otherwise unusable. Further, separate pieces of equipment require additional valuable laboratory space which is typically limited.

There are basically two types of separate mixers. One consists of a platen having grooves for receiving the specimen tubes. The platen and tubes are tilted or rocked slowly back and forth to mix the cells in the individual specimens. The second consists of a set of rollers between which the specimen tubes are manually placed. This second mixer mixes by simultaneously rotating and tilting the rollers.

Apparatus are also known which overcome some of the above-mentioned disadvantages of using separate mixers and samplers by including a mixing paddle in the sampler. The specimen tubes in such apparatus are open so that the mixing paddle can be introduced into the tubes to mechanically stir the specimens. These samplers also have a probe which is dipped into the specimens (after they have been individually mixed by the paddle) to aspirate samples therefrom.

Although open-tube mixer-samplers solve some of the problems arising from the use of separate mixers and samplers, they have other disadvantages. For example, the paddle will carry over blood from one specimen to the next unless it is washed between stirrings or is made of a water- and protein-repellent material. In addition, while inserting open specimen tubes into the mixer-sampler the sampler operator is exposed to the risk of contamination and infection, such as by hepatitis and other similarly transmitted diseases.

Representative patents which are of interest in the field of samplers include U.S. Pat. Nos. 3,607,097, 3,768,526, 3,832,140, 3,883,306, and 3,918,913. Also of interest is U.S. Pat. No. 3,431,886 which shows an apparatus for applying stains to microscopic slides and helical means for moving said slides in the apparatus.

SUMMARY OF THE INVENTION

Among the several objects of the present invention may be noted the provision of apparatus for obtaining samples from specimens of blood or the like contained in a series of closed containers which apparatus thoroughly and gently mixes whole blood specimens before sampling to obtain a uniform distribution of cells within each specimen; the provision of such apparatus in which an operator is not exposed to health hazards such as contamination or infection while samples are being taken; the provision of such apparatus which simplifies the sampling of blood serum; the provision of such apparatus in which the possibility of contaminating one specimen with particles or cells from another is avoided; the provision of such apparatus which easily accommodates specimen tubes of different sizes; the provision of such apparatus in which the possibility of loss or breakage of a specimen container is minimized; the provision of such apparatus which prevents excessive variation in the temperature of the specimens during mixing and sampling; and the provision of such apparatus which is compact, reliable, economical to use, easy to install and operate, and utilizes laboratory space efficiently.

Briefly, apparatus of the present invention comprises means for moving along a predetermined path to a sampling station a series of closed containers containing specimens of blood or the like including a plurality of particles such as cells. When whole blood is being sampled, the moving means also imparts motion to the closed containers while they are moved along the path to obtain a substantially uniform distribution of the particles contained therein. The apparatus includes means for penetrating the closed containers when they reach the sampling station to withdraw specimen samples from the closed containers. Other objects and features will be in part apparent and in part pointed out hereinafter.

BRIEF DESCRIPTION OF THE DRAWINGS

FIG. 3 is a left side elevation of FIG. 1 with a side cover removed;

FIG. 5 is an exploded perspective view of the top portion of the feed screw spacing adjusting means of the invention;

FIG. 6 is an exploded perspective view of the lower portion of the feed screw spacing adjusting means of the invention;

FIG. 7 is a plan view of FIG. 6;

FIG. 8 is an elevation, on an enlarged scale, of the inner and outer needles used in the penetrating means of the invention, with the needles separated to show detail more clearly;

FIG. 9 is a front elevation, on an enlarged scale, of the needle carriage of the invention;

FIG. 10 is a front elevation, on an enlarged scale, of the second carriage of the invention;

FIG. 11 is a plan of the penetrating means of the invention with parts removed;

FIGS. 15A–15C are detailed schematics of the control circuitry of FIG. 15;

FIG. 15D is a semi-diagrammatic representation of the sampler of this invention showing the connections to the control circuitry shown in FIGS. 15A–15C;

Corresponding reference characters indicate corresponding parts throughout the several views of the drawings.

DESCRIPTION OF A PREFERRED EMBODIMENT

Figure 1:
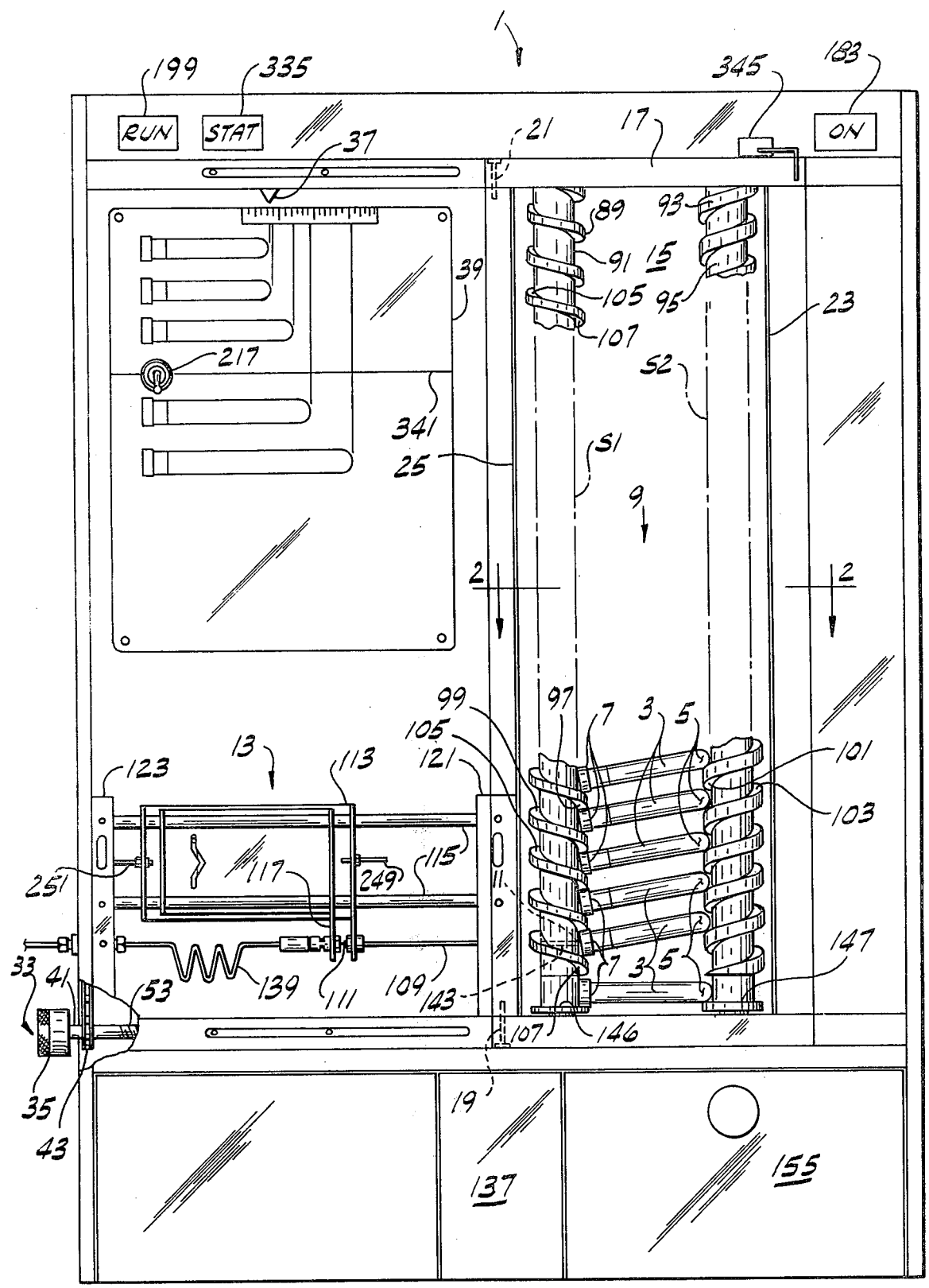
FIG. 1 is a front elevation of sampling apparatus of this invention, with parts broken away.

Referring now to the drawings, sampling apparatus of the present invention is indicated generally at 1. A series of closed containers or specimen tubes 3, typically a series of test tubes 5 closed with rubber stoppers 7 and containing specimens of whole blood, blood serum or the like are moved along a predetermined path 9 to a sampling station 11 by two rotatable feed screws, indicated by reference characters S1 and S2. Feed screws S1 and S2 constitute means for moving closed containers 3 along predetermined path 9 to sampling station 11 and for imparting motion to the closed containers while they are moved along the path to obtain a substantially uniform distribution of the particles contained therein. A penetrating means, indicated generally at 13, penetrates each closed container 3 as it reaches sampling station 11 to withdraw specimen samples therefrom.

Feed screws S1 and S2 are vertical, substantially parallel and spaced from each other such a distance that they engage specimen tubes 3 at longitudinally spaced positions, i.e., at their ends. To load specimen tubes 3 into sampling apparatus 1, screws S1 and S2 are first rotated to such relative positions that the longitudinal axes of specimen tubes 3 will be horizontal when loaded into sampling apparatus 1. Screws S1 and S2 are then rotated to move specimen tubes 3 sequentially from their loading positions downwardly on predetermined path 9 to sampling station 11. As specimen tubes 3 move down path 9 to sampling station 11, they are at all times constrained by screws S1 and S2 to remain on path 9, i.e., screws S1 and S2 define predetermined path 9.

Sampling apparatus 1 has a rear wall 15 disposed behind feed screws S1 and S2 and a transparent door 17 disposed in front of them. Door 17 is hingedly attached to the rest of sampler 1 by two pins, indicated by reference numerals 19 and 21, which define an axis about which door 17 rotates. Door 17 is swung open to permit loading of specimen tubes 3 and is closed while sampler 1 is operating.

Figure 2:
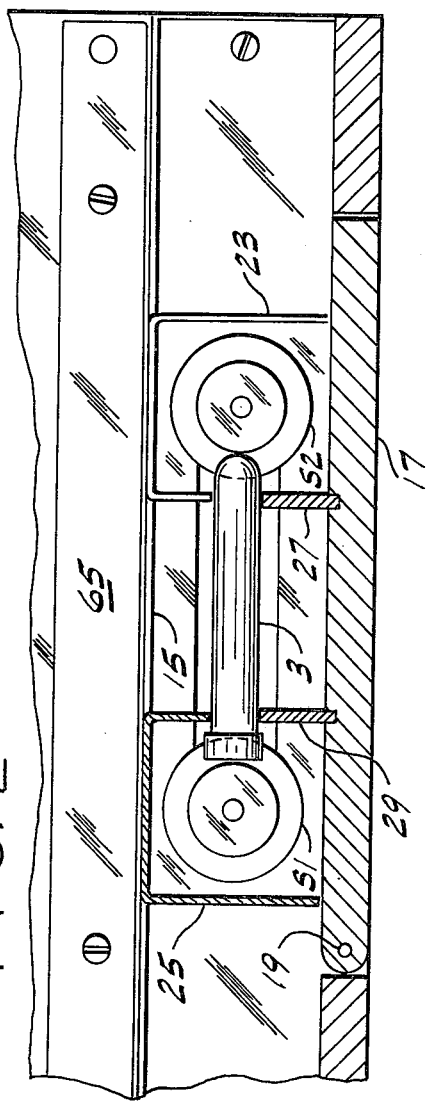
FIG. 2 is a sectional view on line 2—2 of FIG. 1, on an enlarged scale.

The relative locations of wall 15, screws S1 and S2, and door 17 are shown in FIG. 2. A J-shaped rail or support 23 and a J-shaped rail or support 25 are secured to wall 15 intermediate the feed screws. A retainer 27 and a retainer 29 are secured to door 17. Supports 23 and 25 and retainers 27 and 29 extend the length of screws S1 and S2. Rails 23 and 25, screws S1 and S2, rear wall 15 and door 17 constitute means extending along path 9 for enclosing path 9, so that the temperature of specimen tubes 3 can be controlled. Variation in the temperature, of course, can lead to undesirable changes in the specimens.

Support rails 23 and 25 serve another purpose. Because of the pitches of screws S1 and S2 (see FIG. 1), gravity will tend to cause specimen tubes 3 to roll backwards toward rear wall 15, especially as tubes 3 move along predetermined path 9. Support rails 23 and 25 constitute means for retaining closed containers 3 in engagement with feed screws S1 and S2 as they move along predetermined path 9. The pitch arrangement itself prevents tubes 3 from falling out of the apparatus when door 17 is opened and the feed screws are at rest.

The spacing between feed screws S1 and S2 may be adjusted so that specimen tubes 3 of various sizes may be loaded between screws S1 and S2. Of course, all the specimen tubes 3 loaded and sampled during any one sampling cycle are of the same size. That is, the spacing between feed screws S1 and S2 can be adjusted so that specimen tubes of different lengths can be processed, but only one length should be processed per loading-sampling cycle.

Figure 4:
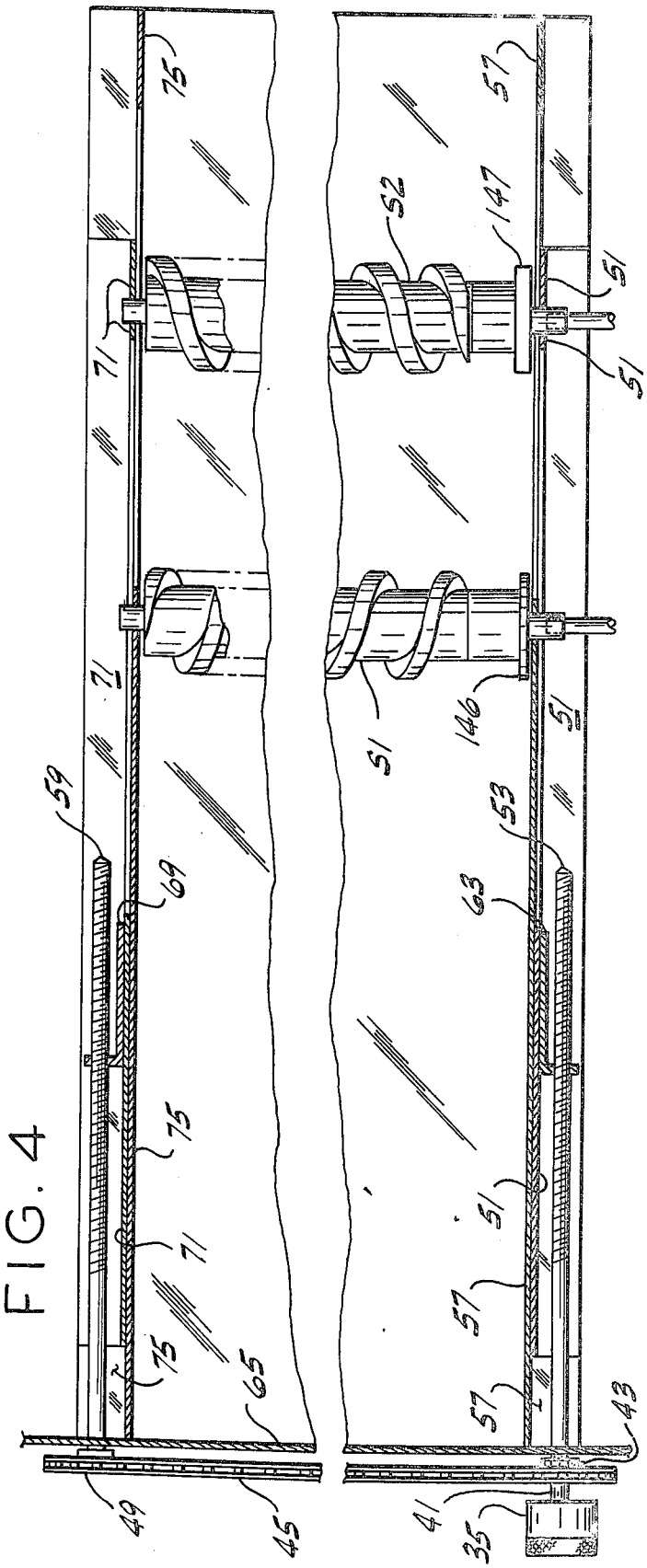
FIG. 4 is a section on line 4—4 of FIG. 3.

Means for adjusting the spacing between feed screws S1 and S2 so that the feed screws may accommodate various sized closed containers 3 is indicated generally at 33. Adjusting means 33 includes a knob 35, a pointer 37, and a scale 39. The spacing between screws S1 and S2 is adjusted by turning knob 35 until pointer 37 is aligned with the proper tube length on scale 39. Knob 35 is secured to a shaft 41 which in turn is secured to a lower sprocket wheel 43. A chain 45 (FIG. 3) engages the sprockets of sprocket wheel 43. Chain 45 also engages the sprockets of an idler sprocket wheel 47 and an upper sprocket wheel 49. Lower sprocket wheel 43 is attached to a threaded rod 53, which is threaded through a lower adjustment bracket 63 (FIG. 4). Lower adjustment bracket 63 is spot-welded to a U-shaped bottom support for screw S2, designated by reference numeral 51 (FIG. 6). The base of screw S2 is rotatably mounted in hole 55 in bottom support 51. Bottom support 51 is slidably mounted in a lower channel 57 which is secured to portions of the chassis of apparatus 1, said chassis being indicated by the reference numeral 65. Channel 57 has a hole 67 in which the base of screw S1 is rotatably mounted.

Likewise upper sprocket wheel 49 is attached to a threaded rod 59, which is threaded through an upper adjustment bracket 69. Upper adjustment bracket 69 is spot-welded to a U-shaped top support for screw S2, designated by reference numeral 71. The top of screw S2 is rotatably mounted in a hole 73 in top support 71. Top support 71 is slidably mounted in an upper channel 75, which is secured to chassis 65. The top of screw S1 is rotatably mounted in a hole 77 in upper channel 75. Together, supports 51 and 71 constitute means for supporting feed screw S2. Rods 53 and 59 and brackets 63 and 69 constitute means for moving said supporting means in channels 57 and 75 to change the spacing between feed screws S1 and S2.

Since channels 57 and 75 are both securely affixed to chassis 65, the position of feed screw S1 is fixed. Supports 51 and 71, together with channels 57 and 75, constitute means for moving screw S2 relative to screw S1. When knob 35 is turned, it turns lower sprocket wheel 43. This motion is transmitted by chain 45 to upper sprocket wheel 49, causing it to turn at the same rate and in the same direction as lower cogwheel 43. The rotation of lower sprocket wheel 43 also rotates threaded rod 53. As threaded rod 53 rotates it causes lower support bracket 63 to move longitudinally with respect to the threaded rod. Since rod 53 is welded to bottom support 51, movement of rod 53 causes bottom support 51 to slide in channel 57, thereby moving the bottom of screw S2 with respect to screw S1. At the same time rotation of upper sprocket wheel 49 causes threaded rod 59 to rotate at the same rate and in the same direction as threaded rod 53. This rotation causes upper support bracket 69 to move in exactly the same direction and at the same rate as lower bracket 63, thereby causing upper support 71 to slide in upper channel 75 synchronously with the sliding of lower support 51 in lower channel 57. Because of this synchronous relationship, the top and base of screw S2 move in the same direction at the same rate, moving screw S2 relative to screw S1 without tilting screw S2.

Bottom channel 57, bottom support 51, threaded rod 53, and bottom support bracket 63 are substantially identical with top channel 75, top support 71, threaded rod 59, and top support bracket 69. The only significant difference between the top and bottom portions of adjusting means 33 is that pointer 37 is attached to top support 71. Pointer 37 is slidably mounted on the outside of channel 75 and is secured to top support 71 by two bolts or screws, indicated by the reference numbers 79 and 80, which pass through an opening 81 in channel 75. As top support 71 moves relative to channel 75, pointer 37 moves along scale 39 to indicate the spacing between screws S1 and S2. The length of opening 81 is chosen so that neither bolt 79 nor bolt 80 strikes the end of opening 81 before the desired spacing between screws S1 and S2 is reached.

Bottom channel 57 has an oblong hole 83, lying directly beneath predetermined path 9, which is wider than specimen tubes 3. Bottom support 51 also has an oblong hole 85 which lies directly beneath predetermined path 9 and is wider than specimen tubes 3. As can be seen from FIG. 7, when bottom support 51 is mounted in channel 57 a composite, oblong hole 87 is formed through both channel 57 and bottom support 51. As bottom support 51 is moved relative to channel 57, thereby changing the spacing between screws S1 and S2, the length of hole 87 changes to correspond to the specimen tube 3 size corresponding to the new screw spacing.

Typically a hospital will buy a large quantity of specimen tubes 3 of the same size. Once the screw spacing of sampler 1 has been adjusted, as described above, to fit the desired size of specimen tube, the spacing is not readjusted unless the hospital begins using a different sized tube. Commercial laboratories, on the other hand, sample many different sized specimen tubes daily. It is quite convenient with sampler 1 to change the screw spacing often to accommodate the different tube sizes.

After the desired screw spacing has been set by means of spacing adjustment means 33, the operator opens door 17 and loads specimen tubes 3 into sampler 1. Feed screw S1 has a helical thread having a helical crest 89 and a helical root 91. Similarly, feed screw S2 has a helical thread having a helical crest 93 and a helical root 95. When the proper spacing between screws S1 and S2 has been set, the opposite ends of specimen tubes 3 rest between adjacent facing portions of the walls of the respective screws. Using the second tube 3 from the top as shown in FIG. 1 as an example, the end of that tube with the rubber stopper rests between a wall portion 97 and a wall portion 99 which portions are adjacent and facing. Likewise, the opposite end of that tube rests between a wall portion 101 and a wall portion 103, which are also adjacent and facing. Preferably the spacing between feed screws S1 and S2 is adjusted so that the spacing between roots 91 and 95 is not less than the length of closed container 3 and the spacing between crests 89 and 93 is not greater than that length.

Root 91 of feed screw S1 is wider than root 95 of feed screw S2. The stoppered end of whole blood specimen tubes is larger than the opposite end, so the width of root 91 is selected to accommodate the stoppers. The width of root 95 is chosen such that the stoppered end of such tubes will not fit into the threads of screw S2, but the opposite end of the specimen tube will. This feature prevents the operator from inadvertently loading whole blood specimen tubes 3 into sampler 1 with the stoppered end facing the wrong way.

On either side of crest 89, feed screw S1 has a wall. The wall on which tubes 3 rest is indicated by reference numeral 105; the other wall by 107. Thus, wall portion 99 is a portion of wall 105 and wall portion 97 is a portion of wall 107. Wall 105 is a machined aluminum surface which is adapted to frictionally engage rubber stoppers 7 of specimen tubes 3 to rotate them about their longitudinal axes thereby mixing the particles in the specimen tubes. If additional friction is desired between specimen tubes 3 and the wall, wall 105 may be knurled.

After specimen tubes 3 are loaded into sampler 1, screws S1 and S2 are rotated to move the tubes along predetermined path 9. The pitch of each feed screw S1 and S2 is substantially constant throughout its length, and the pitches of the feed screws are substantially identical, although they are in opposite directions. Since the crests of screws S1 and S2 are pitched in opposite directions, the screws are rotated in opposite directions to move specimen tubes 3 down along predetermined path 9 to sampling station 11 at its end. As each specimen tube 3 reaches sampling station 11, screws S1 and S2 are rotated so that specimen tubes 3 are tilted, the rubber stoppered ends of specimen tubes 3 being lower than the opposite ends, this rubber-stopped end of each closed container 3 being the puncturable end. Penetrating means 13 then penetrates rubber stopper 7, i.e., the puncturable end of the closed container, and aspirates a sample of the specimen from tube 3. During aspiration tube 3 is held firmly in place by screws S1 and S2, supports 23 and 25, and retainers 27 and 29.

Penetrating means 13 includes a hollow needle 109 having an opening 110 therein through which a specimen sample may be admitted into needle 109, a rod 111 slidably mounted inside needle 109, the outside diameter of rod 111 being slightly smaller than the inside diameter of needle 109, and a reciprocating means indicated generally at 112. Reciprocating means 112 includes an outer sliding carriage 113 to which needle 109 is mounted, two shafts forming a track 115 on which outer carriage 113 is slidably mounted, and an inner sliding carriage 117 on which rod 111 is mounted and which itself is slidably mounted on track 115. Reciprocating means 112 moves carriages 113 and 117 back and forth along track 115 between a retracted position of needle 109, shown in FIG. 12A, and an extend position shown in FIG. 12D. Reciprocating means 112 includes a chain and support drive 129 and a pin 131 secured to the chain of chain-and-sprocket drive 129, which together constitute means for moving carriages 113 and 117 over track 115. Track 115 is secured at one end to a right end block 121 and at the other end to a left end block 123. Carriage 113 has a slot 125 in which pin 131 is slidably mounted. Pin 131 likewise is slidably mounted in a winged V-shaped slot 127 in carriage 117.

Figure 12A:
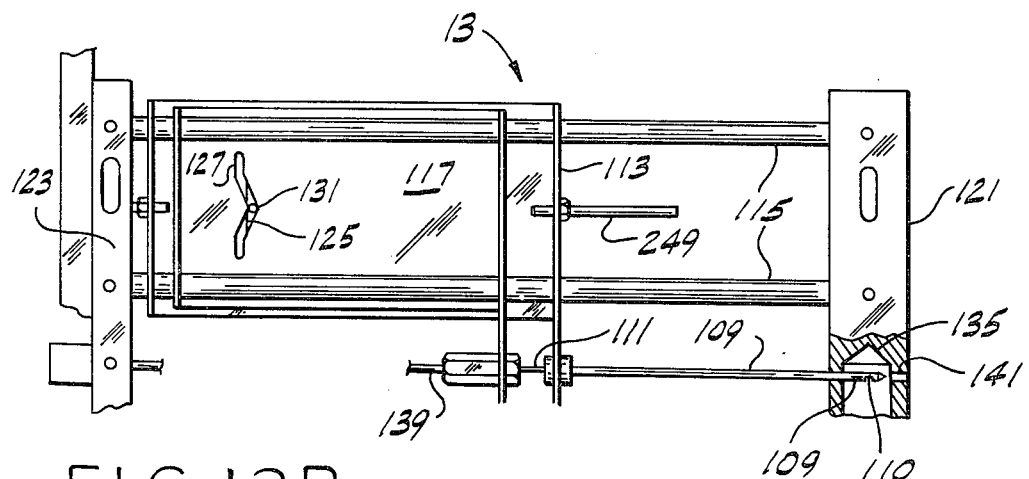
FIGS. 12A–12E are semi-diagrammatic representations, on an enlarged scale, of the operation of the penetrating means of the invention with parts broken away and shown in section.
Figure 12B:
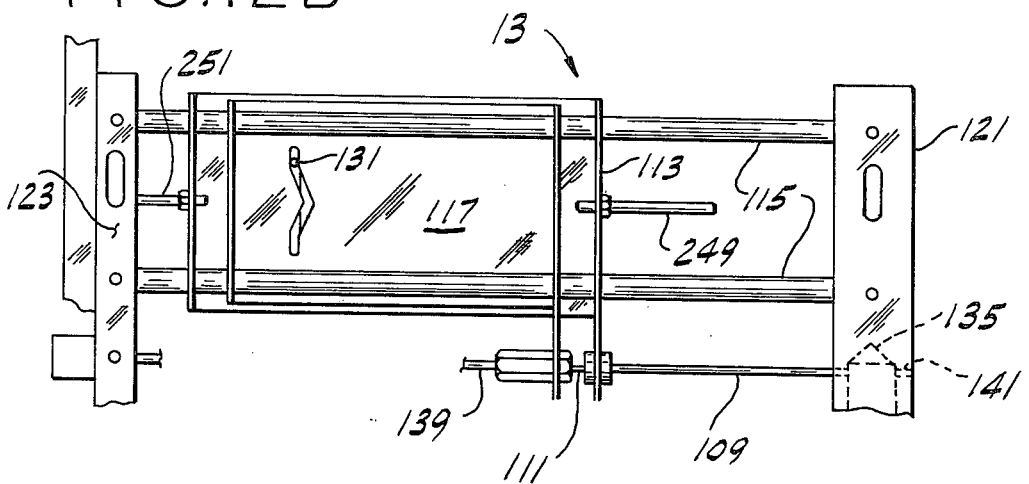
Figure 12C:
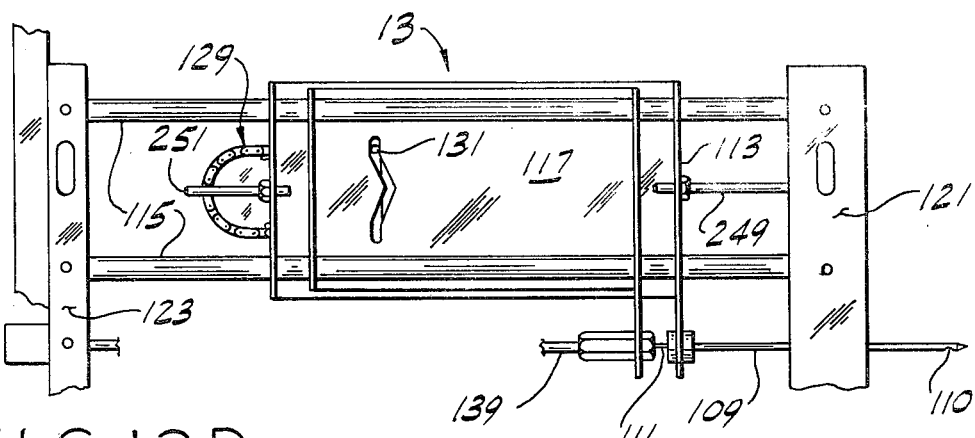
Figure 12D:
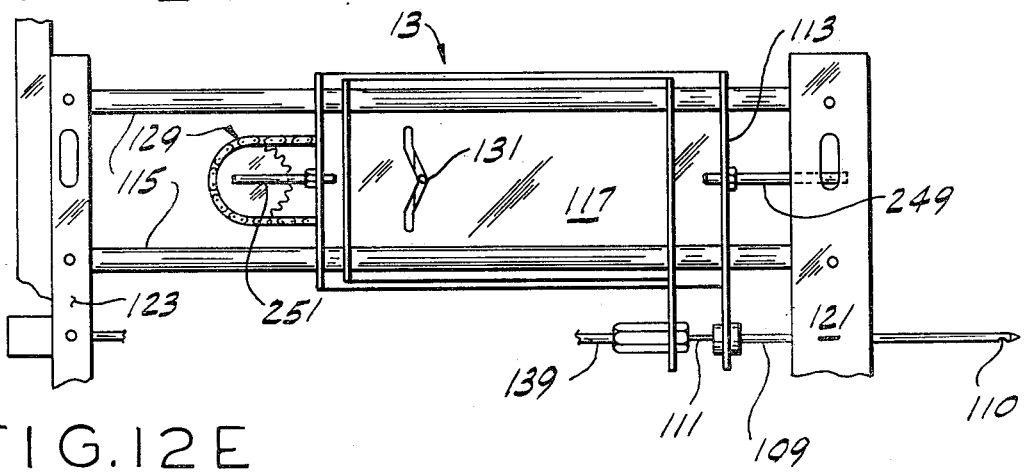
Figure 12E:
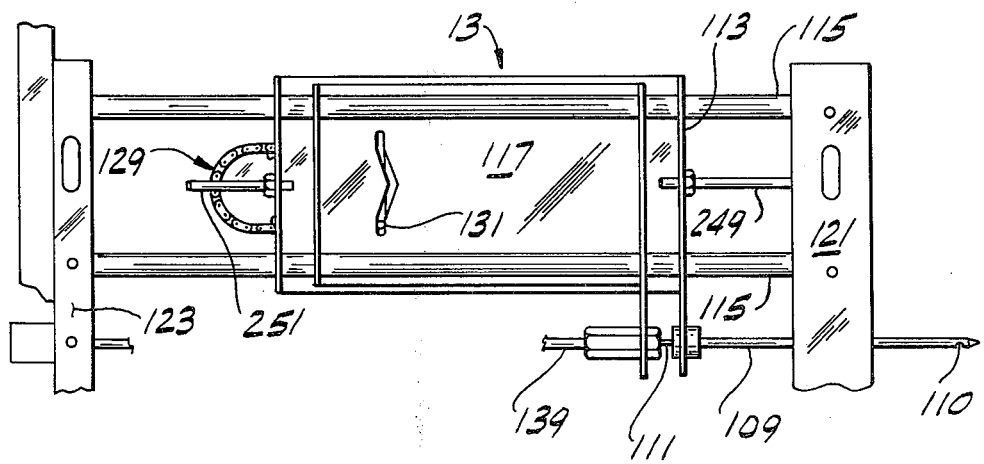

As pin 131 moves along the oblong path defined by chain-and-sprocket drive 129, it moves carriage 113 and 117 between the fully retracted position shown in FIG. 12A and the various extended positions shown in FIGS. 12B–12E. When pin 131 is at the leftmost position along its path, shown in FIG. 12A, it lies in the centers of slots 125 and 127. Due to the shape of slot 127, carriage 117 is then at its leftmost position relative to carriage 113. Of course, the position of rod 111 inside needle 109 is determined by the relative positions of carriages 113 and 117. In this relative position of carriages 113 and 117, rod 111 is retracted slightly inside needle 109, thereby unblocking opening 110 on the side of the tip of needle 109. There is a waste chamber 135 (FIGS. 12A and 12B) in right end block 121 with which needle 109 communicates when at its retracted position so that it may be cleaned and any waste material collected in waste chamber 135. While rod 111 is retracted, needle 109 is backflushed to remove blood contaminants. This backflush waste material passes through needle opening 110 into waste chamber 135 and from there into a waste receptacle 137 in the base of sampler 1. The backflushing material is introduced into needle 109 through a flexible tube 139 and rod 111.

As pin 131 moves toward the top of the rear wheel of chain-and-sprocket drive 129, it moves carriage 117 forward relative to carriage 113. When pin 131 reaches that position shown in FIG. 12B, carriage 117 is at its maximum forward position relative to carriage 113, and rod 111 blocks needle opening 110. As pin 131 moves from its position in FIG. 12B to the top of the front wheel of drive 129, shown in FIG. 12C, it moves carriages 113 and 117 and needle 109 toward their fully extended positions in unison. Needle 109 passes through a hole 141 in right end block 121 and a bore hole 143 extending diametrically through screw S1 and pierces rubber stopper 7 of specimen tube 3 dwelling at sampling station 11 as it moves toward its extended position. Pin 131 then moves forward and down to the position shown in FIG. 12D, which moves carriage 117 back relative to carriage 113, thereby moving rod 111 back to unblock needle opening 110 after rubber stopper 7 has been penetrated. A sample of the specimen in tube 3 is then aspirated through needle opening 110. The sample passes through a longitudinal bore 145 in rod 111 into flexible tube 139, from which it passes to an appropriate sample analyzer (not shown). Pin 131 then continues along its path around drive 129. As it moves to the lower extent of the drive, shown in FIG. 12E, rod 111 moves forward relative to needle 109, blocking needle opening 110 as the needle is removed from specimen tube 3. Needle 109 is moved back to its retracted position by pin 131 to be backflushed in preparation for another sampling cycle.

Of course, a single needle may be used instead of the needle 109 and rod 11 combination and in fact, the results with a single, straight needle are excellent. If there is to be backflushing, however, it is necessary to block hole 141 during this operation. A rotatable sleeve (not shown) fitting inside waste chamber 135 performs this blocking function well.

Figure 13:
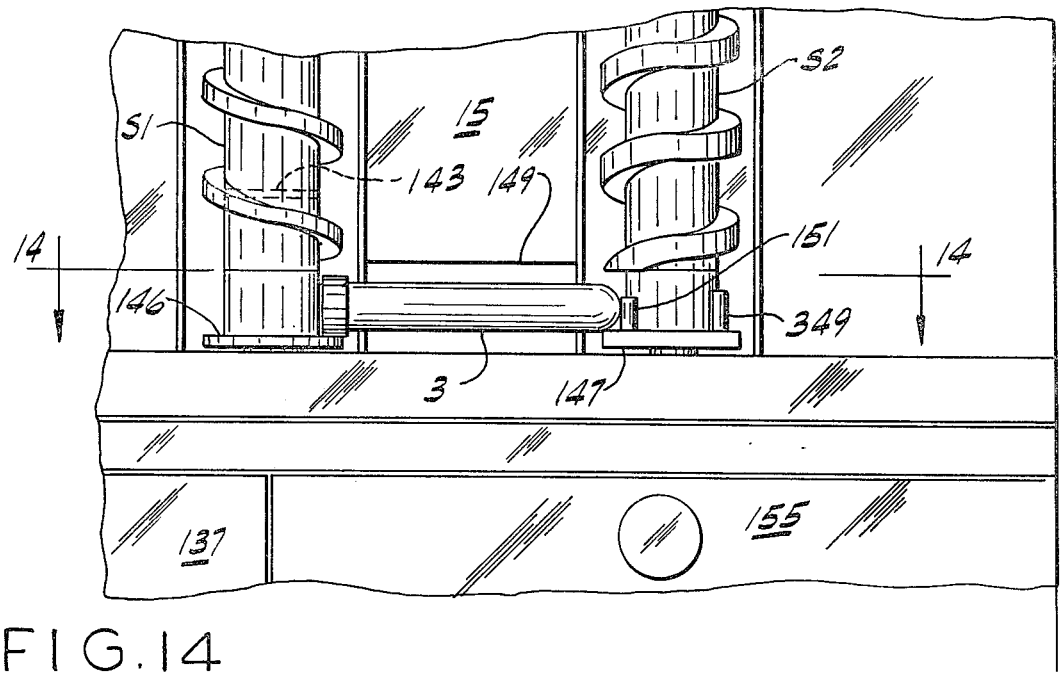
FIG. 13 is an elevation, on an enlarged scale, of a portion of FIG. 1 with parts removed.

A flat collar 146 is fixed to the bottom of screw S1 below sampling station 11 and a flat collar 147 is fixed to the bottom of screw S2. After specimen tube 3 is sampled, screws S1 and S2 rotate, moving tube 3 to the ends of the screw threads where it falls off the threads. Collars 146 and 147 constitute means for interrupting the fall of each closed container 3 in order to allow identification of the container. Collars 146 and 147 hold tube 3 level while screws S1 and S2 continue to rotate. The top surface of collar 146 is knurled, so that as screw S1 rotates tube 3 rotates about its longitudinal axis. Tube 3 has markings thereon (not shown) which identify the specimen contained therein. The time spent by tube 3 on collars 146 and 147 allows identification of tube 3 to be made by a reader (not shown) positioned behind a window 149 in rear wall 15 (FIG. 13). Since tube 3 is rotating as screw S1 rotates, the reader will detect the identifying markings no matter where they are located on the circumference of tube 3. Collar 147 has a pin 151 attached thereto which constitutes means for retaining tube 3 on collars 146 and 147 when door 17 is open.

Figure 14:
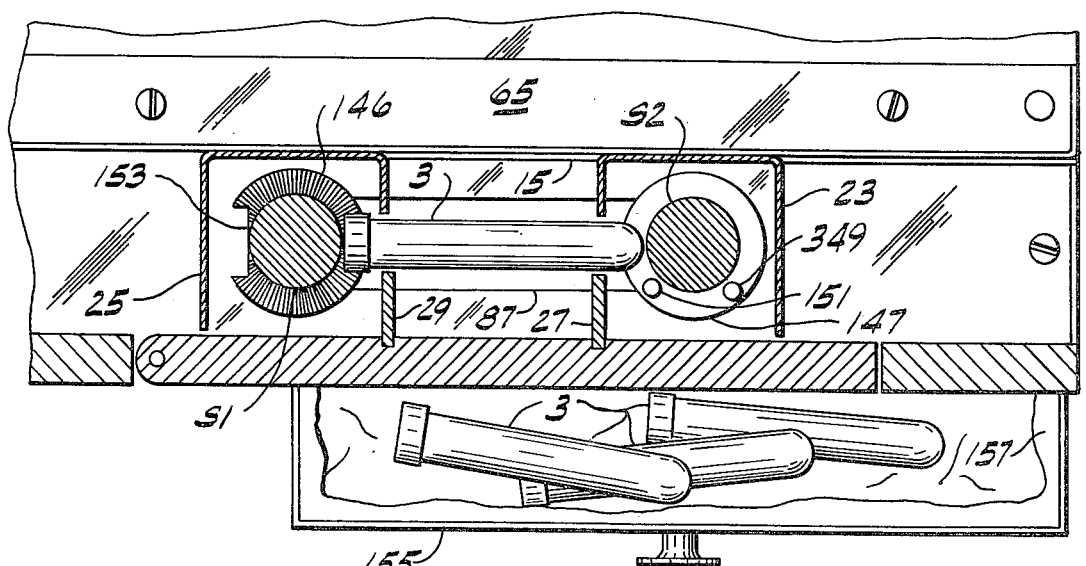
FIG. 14 is a section on line 14—14 of FIG. 13.

Collar 146 has a notch 153 for removing tube 3 from the collars (FIG. 14). When screw S1 rotates so that notch 153 is directly under rubber stopper 7 of specimen tube 3, tube 3 falls through collar 146, through hole 87 in channel 57 and bottom support 51, and into a tube receptacle or drawer 155. Drawer 155 is shown in an open position in FIG. 14 with previously sampled tubes ready to be removed. In operation, drawer 155 is directly under hole 87. Breakage of specimen tubes 3 is reduced by a layer of foam material 157 in the bottom of drawer 155 and by the fact that the rubber stoppered end of each tube 3 falls into drawer 155 first, thus breaking the tubes' fall.

Of course screws S1 and S2 can be extended in length well beyond sampling station 11 to hold sampled specimen tubes 3, thus obviating the need for drawer 155.

Figure 15:
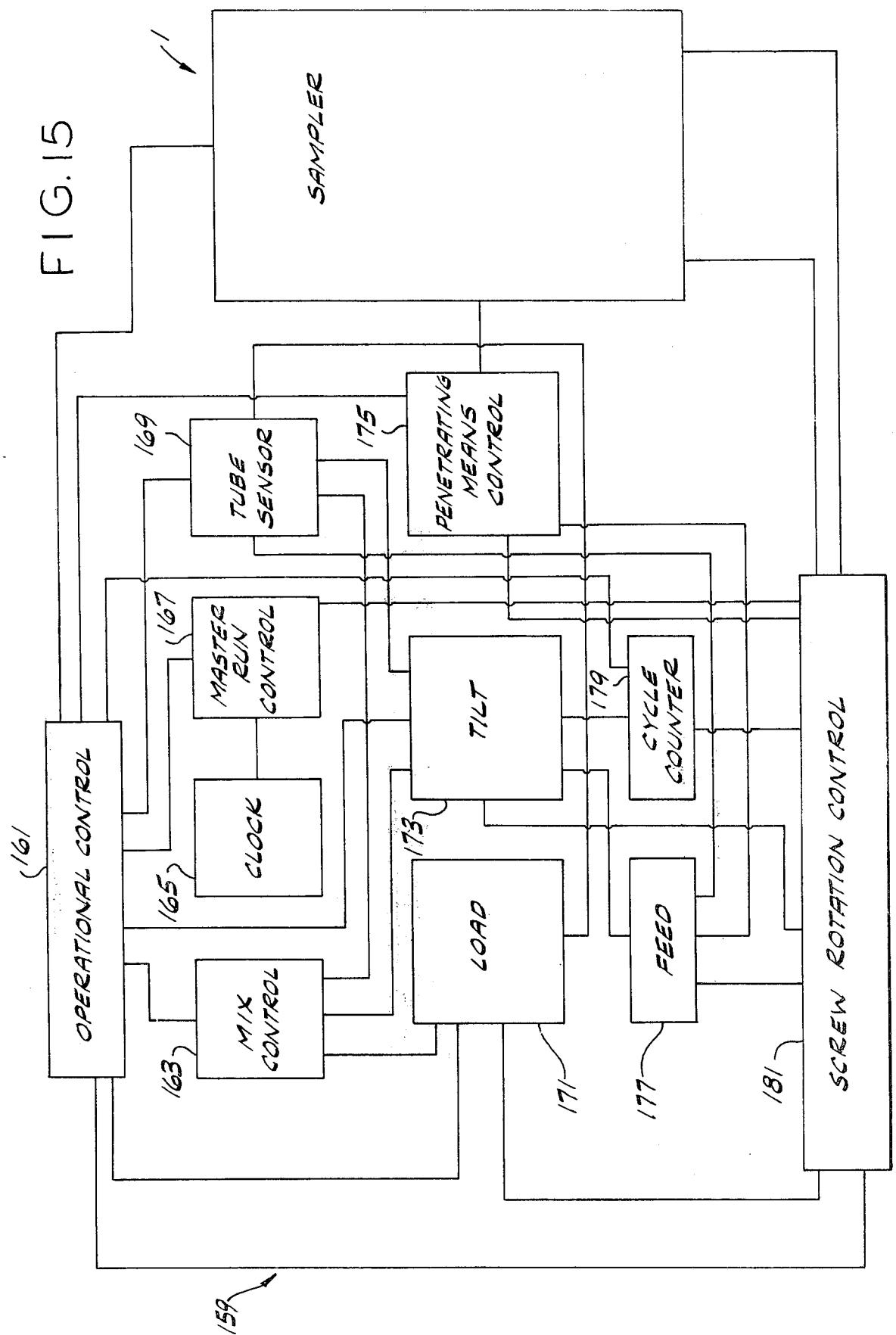
FIG. 15 is a block diagram of the control circuitry of the invention.

The operation of sampler 1 is governed by a control circuit or means indicated generally at 159 (FIG. 15). That is, control means 159 controls the rotation of feed screws S1 and S2 and the operation of penetrating means 13. In part, control means 159 constitutes means for positioning one end of a closed container 3 at sampling station 11 lower than the other end.

Control means 159 includes an operational control section 161, a mix control section 163, a clock 165, a master run control section 167, a tube-sensing section 169, a load section 171, a tilt section 173, a penetrating means control section 175, a feed section 177, a cycle counter 179, and a screw rotation control section 181. Operational control section 161 translates four basic operator actions, viz., pushing one or more of three control buttons and closing door 17, into electrical signals which control the functioning of the other sections of control means 159. Briefly, the functions of the various sections are as follows: Mix control section 163 controls whether sampler 1 mixes and samples (as for whole-blood specimens) or only samples (as for blood serum specimens). Clock 165 provides clock pulses at a frequency of 270 Hz to master run control 167, which governs whether the clock pulses are supplied to screw rotation control section 181. Tube-sensing section 169 governs whether penetrating means 13 is activated. Load section 171 causes screws S1 and S2 to rotate to a point where specimen tubes 3 can be horizontally loaded into sampler 1. Tilt section 173 constitutes means for tilting the closed container 3 at sampling station 11 so that one end of the container is lower than the other end. Specifically, it causes screw S1 to rotate relative to screw S2 to tilt the puncturable end of the container (i.e., rubber stopper 7) lower than the rest of container 3 at sampling station 11 whereby needle 109 may be inserted into the lower end of said container. Penetrating means control section 175 controls the motion of penetrating means 13. Feed section 177 causes screws S1 and S2 to rotate simultaneously at the same rate in opposite directions. Cycle counter 179 controls the amount of mixing that occurs before sampling. Screw rotation control section 181 controls the direction and amount of rotation of screws S1 and S2. The interrelationships among these various sections and their other functions are explained below in the description of the preferred circuit making up control means 159.

It is preferred that the circuitry be TTL or TTL compatible and that circuitry power be supplied at a voltage level of 5 volts. In accordance with convention, a voltage level around 5 volts will hereinafter be called "High" and a voltage level around zero volts will be called "Low". As is well known in the art, if TTL integrated circuits are used to implement the circuit, each should be decoupled between $V_{cc}$ and ground by means of a 0.1 μF disc ceramic capacitor.

Above and to the right of door 17 is an ON switch 183. Pressing ON switch 183 provides power to the circuitry of control means 159. Turning on the power makes a voltage terminal V1 High. Terminal V1 is connected through a resistor R1 and a capacitor C1 to ground. Resistor R1 has a resistance of 1 kilohm and C1 has a capacitance of 50μF. Because of the presence of capacitor C1, the voltage measured between resistor R1 and capacitor C1 takes some time to go from Low to High. This varying voltage is supplied to an inverter 185. While the input voltage level is less than about 2 volts, the output of inverter 185 stays High, but above 2 volts it goes Low.

The output of inverter 185 is supplied to an inverter 187, which causes the output of inverter 187 to be momentarily Low and to then go High as the output of inverter 185 goes Low. This temporary Low is supplied on a line L1 to the various sections of control means 159 to set the circuit for operation, as is described below.

The Low on line L1 is supplied to a binary counter 189. Specifically the Low appears on the cathode side of a diode D1 connected to the load terminal of counter 189, which along with the other binary counters described below is a Texas Instruments Type N74193 synchronous 4-bit binary counter with parallel load. A Low on the cathode side of diode D1 sends the load terminal Low and loads 1111 into the counter. The 1's output of binary counter 189, designated by the reference numeral 191, goes High upon loading.

A second voltage source V2 is connected through a resistor R2 to an inverter 193 causing its output to be Low. The Low output of inverter 193 is supplied to a NAND gate G1, which causes its output to be High, which output is supplied to a NAND gate G2. The High on output 191 of counter 189 is supplied by a line L2 to the other input of NAND gate G2 causing its output to be Low. This Low output is supplied to an inverter 195 causing its output, which is supplied through a 1-kilohm resistor R3 to the base of a 2N1711-type transistor Q1, to be High. The collector of Q1 is connected to a 5-volt voltage source V3 through an indicator lamp 197. The emitter of Q1 is connected to ground. The High on the base of Q1 causes Q1 to conduct, thereby lighting lamp 197, which lights the surface of a momentary contact, push-button RUN switch 199. The face of switch 199 is shown in FIG. 15D and the switch itself is shown in FIG. 15A.

The High on output 191 of counter 189 is also supplied by line L2 to one of four inputs, designated by the reference numeral 201, of a NAND gate G3, which is part of master run control 167. The other three inputs of NAND gate G3 are designated 203, 205, and 207.

The momentary Low on line L1 is also supplied to an input 209 of mix control section 163. Input 209 is one of three inputs to a NAND gate G4, the other two being designated 211 and 213. Mix control section 163 is used only when blood serum or the like is being sampled. A switch 217 mounted on the front of scale 39 is thrown to the ON position when whole blood is being sampled and thorough mixing is desired. Only when switch 217 is OFF does mix control section 163 function.

Figure 15A:
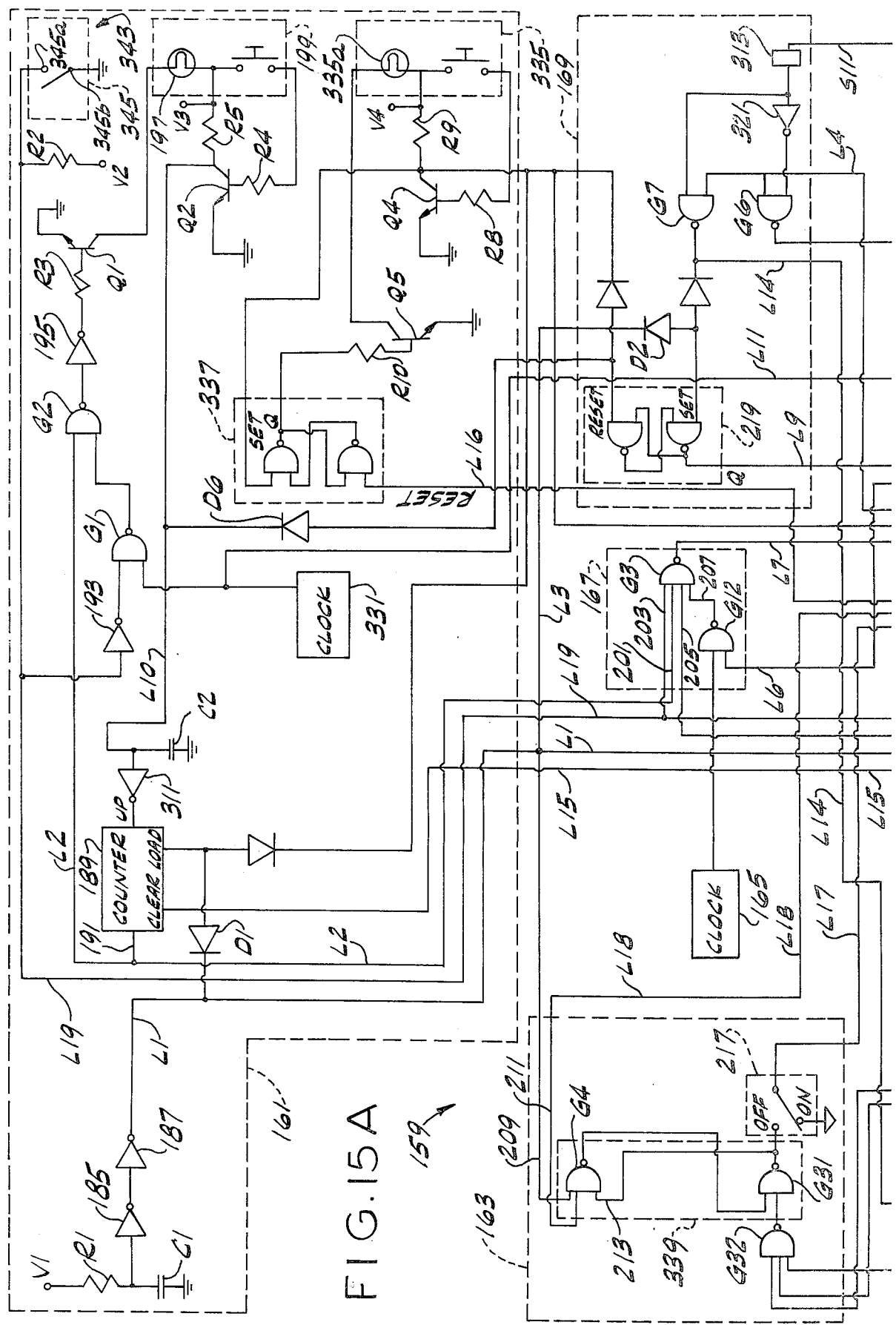
Figure 15C:
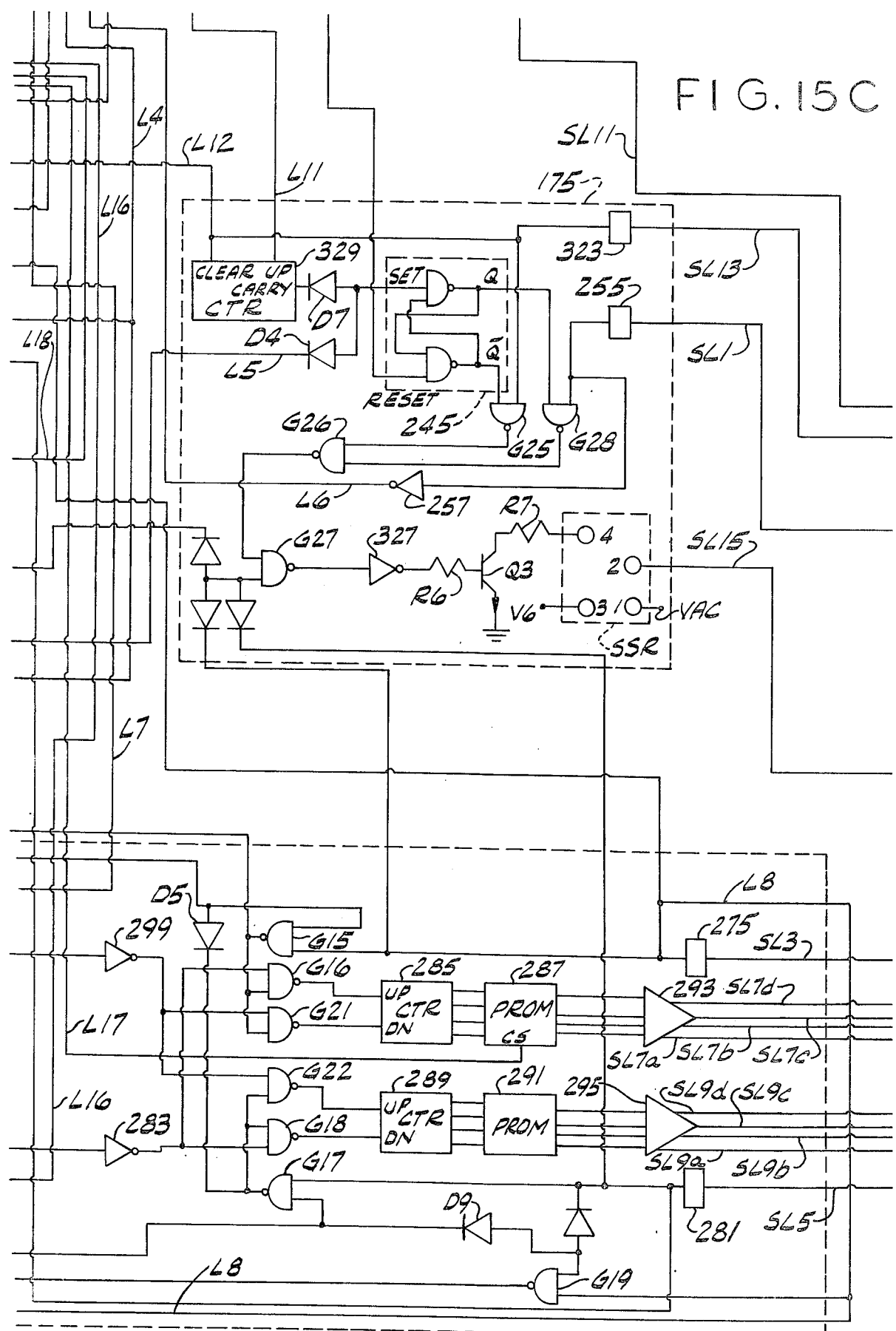

The operation of control means 159 is best seen when switch 217 is ON, as is shown in FIG. 15A. The differences in operation when that switch is OFF are explained later. If switch 217 is ON, the High on input 209 has no effect on the other sections of control means 159.

The momentary Low on line L1 is supplied to tube-sensing section 169. Specifically, the Low on line L1 is supplied via a line L3 and a diode D2 to the set input of a latch circuit 219 in tube-sensing section 169. The momentary Low on the set input sets the Q output of latch 219 high.

The momentary Low on line L1 is also supplied to tilt section 173 to set a latch 221 there. The Low on line L1 is supplied via a diode D3 to the set input of latch 221, thereby setting the Q output High and $\overline{Q}$ output Low. The $\overline{Q}$ output is supplied to one input, designated 223, of a three-input NAND gate G5. The other two inputs of NAND gate G5 are designated 225 and 227. Since input 223 of NAND gate G5 is Low, its output is High. This High output is supplied to input 205 of NAND gate G3 is master run control section 167 and to an inverter 229. Inverter 229 supplies a Low output to tube-sensing section 169 and feed section 177.

Tube presence checking section 169 includes two NAND gates, designated G6 and G7, each having an input connected to a line L4. The Low output from inverter 229 is supplied on line L4 to NAND gates G6 and G7, causing their outputs to be High. The Low output of inverter 229 is also supplied on line L4 to one input of a NAND gate G8 in feed section 177, causing the output of gate G8 to be High.

The Low $\overline{Q}$ output of tilt section latch 221 is also supplied to a NAND gate G9, ensuring that its output is High. This High output is supplied to one of four inputs, designated by the reference numeral 231, of a Down NAND gate G10 in screw rotation control section 181. The other three inputs of Down gate G10 are designated 233, 235 and 237. The Low on line L1 is supplied to input 235 of Down gate G10, ensuring that its output is High. The High output of Down gate G10 is supplied to an input 239 of an Up NAND gate G11. The other two inputs of Up gate G11, designated by the reference numerals 241 and 243, are normally High when On Switch 183 is pushed. Therefore the output of Up gate G11 is Low.

The Low on line L1 is supplied via a line L5 and a diode D4 to the set input of a latch 245 in penetrating means control section 175 thereby setting the Q output of latch 245 High and the $\overline{Q}$ output Low.

The Low on line L1 is also supplied to the set input of a latch 247 in feed section 177, setting the Q output of latch 247 High and the $\overline{Q}$ output Low.

Thus, it can be seen that the effect of the momentary Low on line L1 is to set the latches in the various sections of control circuit 159 in preparation for operation of sampler 1. Operation of sampler 1 depends not only upon the status of these latches, however, but also upon the position of pentrating means 13.

Figure 16:
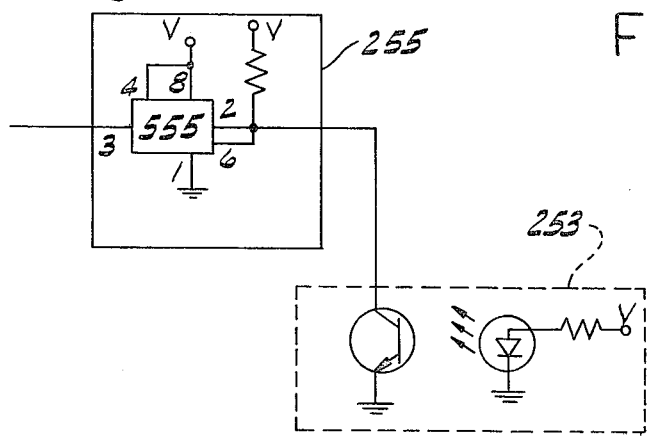
FIG. 16 is a schematic of a buffer circuit used in this invention.

Penetrating means 13 includes a right bolt 249 and a left bolt 251 mounted on the right and left ends of carriage 113. Left bolt 251 interrupts an optical source and sensor circuit 253 in left end block 123 when penetrating means 13 is in the retracted position. The Texas Instruments Type TIL 138 Source and Sensor Assembly works well as optical circuit 253. Of course other lamps and photocells or mechanical switches could be used to perform the same function. The TIL 138 Source and Sensor Assembly includes a Texas Instruments Type TIL 32 gallium arsenide infrared-emitting diode and a Type TIL 78 N-P-N silicon phototransistor. The phototransistor of optical circuit 253 is connected by a sampler-to-circuit line SL1 to a buffer circuit 255, the output of which is High when optical circuit 253 is not interrupted and Low when it is. This buffer, as well as other buffer circuits described below, can be a circuit as shown in FIG. 16. Buffer 255 has as its main component a Type 555 integrated circuit, which is connected as shown in FIG. 16 to the collector of the phototransistor of optical circuit 253.

When bolt 251 is in optical circuit 253, i.e., penetrating means 13 is in its fully retracted position, the output of buffer 255 is Low. This Low output is supplied to an inverter 257 which supplies a High on a line L6 to a NAND gate G12, in master run control section 167. The other input to gate G12 is the 270 Hz output of clock 165. The output of gate G12 is accordingly a 270 Hz clock output. This clock output is supplied to input 207 of NAND gate G3. Since the other three inputs of gate G3 are High, the output of gate G3 is also a clock output of 270 Hz clock pulses.

This output of master run control 167 is supplied on a line L7 to a NAND gate G13, a NAND gate G14 and the "up" clock input of a binary counter 259 in screw rotation control section 181. Counter 259 is cascaded with two other binary counters, designated by the reference numerals 261 and 263, to form an accumulator 265 having the capacity to count at least to 560.

The other input to NAND gate G13 is the Low output of "up" NAND gate G11, so the output of gate G13 is High. That is, clock pulses do not pass through gate G13. The result is that the circuitry which would cause screws S1 and S2 to turn so that specimen tubes 3 would go "Up" is not activated. For ease of illustration, hereinafter the direction of rotation of either feed screw will be referred to as "up" if the ends of specimen tubes 3 resting in that screw will be moved up along predetermined path 9 by that rotation and "down" if the rotation will move them down. Since screws S1 and S2 are oppositely pitched, the up direction of rotation for screw S1 is opposite that of screw S2.

Screws S1 and S2 have positioning disks 267 and 269 attached to their respective bases. Positioning disk 267 has a single hole (not shown) near its circumference which functions as a reference point. An optical sensor circuit 273, identical to circuit 253 described above, is mounted adjacent positioning disk 267 with the rim of disk 267 interrupting optical circuit 273. As disk 267 rotates with screw S1 it brings its positioning hole into alignment with optical circuit 273 once each revolution, thereby closing optical circuit 273. The phototransistor of optical circuit 273 is connected by a sampler-to-circuit line SL3 to a buffer 275 in the same way as optical circuit 253 is connected to buffer 255, which is described above. When the positioning hole of disk 267 is aligned with optical gate 273, the output of buffer 275 is High; otherwise it is Low. Likewise, positioning disk 269 has a positioning hole (not shown) alignable with an optical sensor circuit 279, which optical circuit is connected by a sampler-to-circuit line SL5 to a buffer 281 which has a High output when the positioning hole is aligned in gate 279. When both holes are aligned in their respective optical circuits, screws S1 and S2 are positioned such that specimen tube 3 is in the position to be sampled, i.e., tube 3 is tilted such that the end with rubber stopper 7 is lower than the opposite end. Additionally, when screw S1 is in this position, needle 109 can pass unobstructed through bore 143 in screw S1 and pierce rubber stopper 7. That is, positioning disks 267 and 269 together with optical sensor circuits 273 and 279 constitute means for aligning bore 143 with needle 109 when a closed container 3 is at sampling station 11 thereby permitting movement of the needle through feed screw S1 in order to penetrate the puncturable end of said container.

Normally when ON button 183 is pushed, screw S1 will not be aligned with its associated optical circuit but screw S2 will be. Thus, in the start up process the output of buffer 281 will be High and the output of buffer 275 will be Low. The Low output of buffer 275 is supplied to a NAND gate G15 causing its output to be High. The High output of gate G15 is supplied to a NAND gate G16. Likewise, the output of the other screw buffer circuit, buffer 281, is supplied to a NAND gate G17. The other input of gate G17 is supplied from the Q output of latch 247 in feed section 177 and is also High. The output of gate G17 is, therefore, Low, which is supplied to a NAND gate G18.

The other inputs to gates G16 and G18 are clock pulses supplied from gate G14 by way of an inverter 283. Since one input of gate G18 is Low, its output is High. This has the effect of freezing or preventing rotation of screw S2. On the other hand the non-clock input to gate G16 is High and its output is clock pulses. These pulses are supplied to the up clock input of a binary counter 285. The outputs of binary counter 285 are supplied to a 256 bit, programmable read-only memory (PROM) 287. PROM 287 is a Texas Instruments type SN74S288N read-only memory having a 32 word by eight bit memory matrix.

If screw S2 is not properly aligned, the output of gate G18 will also be clock pulses. These are supplied to the down clock input of a binary counter 289, identical to counter 285. The four outputs of binary counter 289 are supplied to a PROM 291 of the same type as PROM 287. PROMs 287 and 291 are programmed to control the switching sequences for the inputs to two stepper motors, indicated at M1 and M2, attached to screws S1 and S2, each adapted to independently rotate its associated feed screw. More specifically, the first four outputs of PROM 287 are supplied to an amplifier 293 which supplies the amplified signals to stepper motor M1 attached to screw S1 on four lines designated SL7a–SL7d. Motor M1 is an M-series stepper motor sold under the trade designation "Slo-Syn" by Superior Electric Company, Bristol, Connecticut. The switching input sequence of motor M1 is such that screw S1 will advance 0.9° per step of the motor. Likewise the first four outputs of PROM 291 are supplied to an amplifier 295 which supplies the amplified signals on four lines designated SL9a–SL9d to stepper motor M2 attached to screw S2. Motor M2 is also a "Slo-Syn" stepper motor, and it advances screw S2 0.9° per step of the motor. Motor M1 is manufacturer's type MO61-FD02. In general, therefore, screw rotation control section 181 constitutes means for controlling energization of motors M1 and M2.

The program set forth below is for both PROM 287 and PROM 291. Only the first 16 words and the first four bits of each word are used.

| DECIMAL | ADDRESS |   |   |   |   | DATA |     |     |     |
|---------|---------|---|---|---|---|------|-----|-----|-----|
|         | A       | B | C | D | E | D01  | D02 | D03 | D04 |
| 0       | 0       | 0 | 0 | 0 | 0 | 1    | 0   | 1   | 0   |
| 1       | 1       | 0 | 0 | 0 | 0 | 1    | 0   | 0   | 0   |
| 2       | 0       | 1 | 0 | 0 | 0 | 1    | 0   | 0   | 1   |
| 3       | 1       | 1 | 0 | 0 | 0 | 0    | 0   | 0   | 1   |
| 4       | 0       | 0 | 1 | 0 | 0 | 0    | 1   | 0   | 1   |
| 5       | 1       | 0 | 1 | 0 | 0 | 0    | 1   | 0   | 0   |
| 6       | 0       | 1 | 1 | 0 | 0 | 0    | 1   | 1   | 0   |
| 7       | 1       | 1 | 1 | 0 | 0 | 0    | 0   | 1   | 0   |
| 8       | 0       | 0 | 0 | 1 | 0 | 1    | 0   | 1   | 0   |
| 9       | 1       | 0 | 0 | 1 | 0 | 1    | 0   | 0   | 0   |
| 10      | 0       | 1 | 0 | 1 | 0 | 1    | 0   | 0   | 1   |
| 11      | 1       | 1 | 0 | 1 | 0 | 0    | 0   | 0   | 1   |
| 12      | 0       | 0 | 1 | 1 | 0 | 0    | 1   | 0   | 1   |
| 13      | 1       | 0 | 1 | 1 | 0 | 0    | 1   | 0   | 0   |
| 14      | 0       | 1 | 1 | 1 | 0 | 0    | 1   | 1   | 0   |
| 15      | 1       | 1 | 1 | 1 | 0 | 0    | 0   | 1   | 0   |

For each clock pulse supplied from NAND gate G16 to counter 285, the output of counter 285 increases by one thereby addressing the next word in PROM 287. This changes the outputs of PROM 287 such that stepper motor M1 advances one step (0.9°), rotating screw S1 down. Likewise, if screw S2 is not properly aligned, clock pulses are supplied from NAND gate G18 to the down clock input of counter 289, the output of which decreases by one, thereby addressing the preceding word in PROM 291. The output of PROM 291 thus causes stepper motor M2 to retreat one step, rotating screw S2 down. Once screw S2 is properly aligned, as discussed above, NAND gate G18 does not supply additional clock pulses to counter 289, so stepper motor M2 is stopped, thereby stopping rotation of screw S2.

Control means 159 includes a NAND gate G19 which constitutes means for changing the direction of rotation of screws S1 and S2 in order to move one end of closed containers 3 relative to the other end thereby to mix the particles in the specimens. When both screws are properly aligned, both inputs to NAND gate G19 are High, causing its output to be Low. The Low output of gate G19 is supplied to input 241 of up NAND gate G11, making its output High. This High output is supplied to input 233 of down NAND gate G10, making its output Low. As a result the up part of the circuitry is activated and the down part of the circuitry is deactivated.

In addition, proper alignment of screw S1 causes a High output from buffer 275 to be supplied on a line L8 to a NAND gate G20, the other input of which is already High. The resulting Low output is supplied to an inverter 297. The High output of inverter 297 is supplied to the clear inputs of accumulator 265 which clears all the accumulator outputs.

The High output of "up" gate G11 is also supplied to NAND gate G13, the other input of which is clock pulses from master run control section 167. Clock pulses are supplied from gate G13 to an inverter 299 which supplies clock pulses to a NAND gate G21 in the screw S1 circuitry and to a NAND gate G22 in the screw S2 circuitry. The Low output of gate G17 is supplied to the other input of gate G22, however, so clock pulses are prevented from reaching counter 289, thereby freezing screw S2. The Low output of gate G17 is also supplied, via a diode D5 to one input of gate G15, causing its output to be High. This output of gate G15 is supplied to the other input of gate G21, resulting in its output being clock pulses. These clock pulses are supplied to the down clock input of counter 285, causing screw S1 to be rotated "up". As soon as the screw S1 positioning hole leaves optical gate 273, the output of buffer indicator circuit 275 goes Low, removing the "clear" signal from accumulator 265, allowing it to count each clock pulse, and thus each step up of screw S1.

After screw S1 moves up 160 steps, the outputs of accumulator 265 corresponding to counts of 32 and 128 go High. These outputs are supplied to two inputs, designated by the reference numerals 301 and 303, of a NAND gate G23 in Load section 171. The other two inputs of gate G23 are designated by the reference numerals 305 and 307. Input 307 is High because it is connected to the Q output of tube sensing latch 219. Input 305 is also High when screw S1 is rotating "up". Once screw S1 has completed the 160 steps up, therefore, the output of gate G23 goes Low. This low output is supplied to an inverter 309 which supplies a High output to the clear input of counter 189 in operational control section 161. Output 191 of counter 189 immediately goes Low, causing input 201 of gate G3 to go Low, which stops the supply of clock pulses to screw rotation control section 181 and, thus, also stops rotation of screw S1. The Low on output 191 of counter 189 is also supplied to NAND gate G2 causing its output to go High, which causes the output of inverter 195 to go Low turning off "RUN" light 197. Thus, screw rotation control section 181 and load section 171 constitute means for rotating screws S1 and S2 to a loading position and maintaining them there so that specimen tubes 3 can be loaded into sampler 1.

Screws S1 and S2 are now in the proper position for loading specimen tubes 3 into sampler 1. Door 17 is opened and the desired number of tubes 3 are inserted horizontally between screws S1 and S2. Door 17 is then closed and RUN button 199 is pushed, which connects a 5-volt source V3 through a 1K resistor R4 to the base of an n-p-n transistor Q2. The collector of transistor Q2 is connected to voltage source V3 through a 10K resistor R5. Its emitter is connected to ground. Pushing RUN button 199 once causes transistor Q2 to conduct, bringing the voltage of the collector Low. This Low is supplied via a diode D6 to the reset input of tube sensing latch 219 causing its Q output to go Low. This Low is supplied on line L9 to input 307 of NAND gate G23 in load section 171, resulting in the removal of the clear signal from counter 189 in operational control section 161. The Low on the collector of transistor Q2 is also supplied via a line L10 to an inverter 311 isolated from ground by a 0.1µF capacitor C2. The output of inverter 311 thereupon changes from Low to High. This output is supplied to the up clock input of counter 189, causing output 191 of counter 189 to go High. As described above, this causes RUN light 197 to come on and permits clock pulses to pass from master run control section 167 to screw rotation control section 181.

Pushing RUN button 199 a second time turns sampler 1 off. Capacitor C2 immediately discharges through transistor Q2 and then slowly recharges through resistor R5 after RUN button 199 is released. This supplies a clock pulse to counter 189 causing output 191 to go Low. This Low prevents clock pulses from passing through master run control section 167, thereby turning the apparatus off.

If RUN button 199 has only been pushed once, the output of gate G15 is High, the output of gate G17 is Low and screw S1 is therefore free to resume its upward rotation while screw S2 remains stationary, thereby moving one end of specimen tubes 3 relative to the other end, which movement mixes the particles in the specimens. That is, screw rotation control section 181 constitutes means for rotating screw S1 at a rate which differs from the rate of rotation screw S2, thereby mixing the particles in the individual specimen tubes 3. After screw S1 rotates up an additional 160 steps, i.e., 320 steps from alignment in optical circuit 273, the outputs of accumulator 265 corresponding to 320 steps go High. These two High outputs are supplied to a NAND gate G24. The third input of gate G24 is supplied from the Q output of feed latch 247 and is also High, causing the output of gate G24 to go Low. This Low output is supplied to input 237 of "down" gate G10 causing its output to go High, which in turn causes the output of "up" gate G11 to go Low. As a result screw S1 reverses direction and starts rotating down. Thus, screw rotation control section 181 also constitutes means for varying the direction of rotation of screw S1 which also causes mixing of the particles in specimen tubes 3. After screw S1 has moved down 64 steps, the output of NAND gate G24 goes High. This Low to High transition is supplied to the up clock input of cycle counter 179, which thereupon counts one mixing cycle. Screw S1 continues to move down until its positioning hole is again aligned with optical circuit 273. When this happens the output of buffer 275 goes High which clears accumulator 265 and, by means of NAND gate G19, reverses the direction of rotation of screw S1. Screw S1 moves up for 320 steps and then reverses direction and moves back down 320 steps. Again mix cycle counter 179 counts a cycle. This up and down motion of screw S1 causes the specimen tubes 3 to be titled up and down, since screw S2 is stationary, thereby mixing the particles contained in the specimens. It can be seen, therefore, that screw rotation control section 181 constitutes means for selectively rotating screw S1 320 steps clockwise and 320 steps counterclockwise with respect to its longitudinal axis while screw S2 is not simultaneously rotating a like number of steps. The particles in the specimens are also mixed somewhat by the simultaneous rotation of tubes 3 about their longitudinal axis caused by the frictional engagement of rubber stoppers 7 with wall 105 as discussed supra. Since each of stepper motors M1 and M2 rotates its respective feed screws 0.9° per step, screw S1 is rotated 288° by the 320 steps, which is a partial revolution.

Mix cycle counter 179, which constitutes means for stopping the selective rotation of screw S1 after a predetermined number of partial revolutions, is set so that after sixteen complete mixing cycles it supplies a Low to the reset input of tilt section latch 221, which causes its $\overline{Q}$ output to go High. Of course, the number of mix cycles can be varied, the number of cycles depending upon the amount of mixing desired. This High output is supplied to input 223 of NAND gate G5. The other inputs to gate G5 are also High because at this point screws S1 and S2 are both aligned with their respective optical sensing circuits. Thus, the output of NAND gate G5 is Low, and this Low, supplied to gate G3, stops clock pulses from leaving master run control section 167, thereby stopping rotation of screw S1 by stopping motor M1. At this point in the sampling cycle, one of the specimen tubes 3 is at sampling station 11 tilted with its rubber stoppered end lower than the rest of the tube. Cycle counter 179, tilt section 173 and master run control section 167 constitute means, therefore, for stopping motors M1 and M2 when this tube reaches sampling station 11 after mixing, in order to cause it to dwell at sampling station 11.

Figure 17:
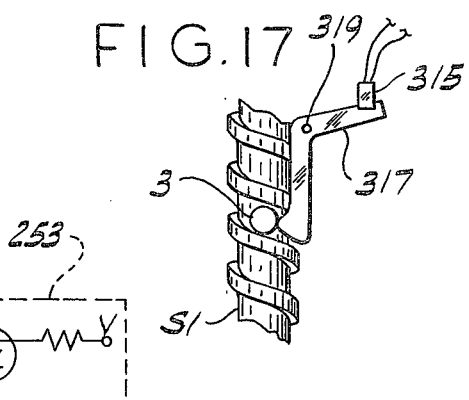
FIG. 17 is a semi-diagrammatic representation of a last tube sensor used in this invention.

The Low output of NAND gate G5 is also supplied to inverter 229. The High output of inverter 229 is supplied on Line L4 to gages G6 and G7 in tube-sensing section 169 and to gate G8 in feed section 177. The other input to gate G7 is connected to a buffer 313, identical to buffers 255, 275 and 281. The input of buffer 313 is connected by a sampler line SL11 to the collector of the phototransistor of a Type TIL 138 optical sensing circuit designated 315. As can best be seen in FIG. 17, a flat elbow-shaped piece 317 interrupts the passage of light through optical circuit 315 when specimen tube 3 is at sampling station 11. On the other hand, when specimen tube 3 is not at the sampling station, elbow-shaped piece 317 pivots around a pivot point 319 and unblocks optical gate 315. If specimen tube 3 is present at sampling station 11, the output of buffer 313 is Low; if not, it is High.

If specimen tube 3 is at sampling station 11 after the mixing has been completed, the Low output of circuit 313 is supplied to the other input of NAND gate G7 and to an inverter 321. The High output of inverter 321 is supplied to NAND gate G6, causing its output to be Low. The Low output of gate G6 is supplied to the reset input of latch 245 in penetrating means control section 175, causing its $\overline{Q}$ output to go High and its Q output to go Low. The $\overline{Q}$ output of latch 245 is supplied to one input of a NAND gate G25. The other input of gate G25 is supplied from a buffer circuit 323 whose output is High unless penetrating means 13 is in its fully extended position.

Buffer 323 is connected by a line SL13 to an optical sensing circuit 325 which determines whether penetrating means 13 is in its fully extended position as follows: Right bolt 249, attached to the right end of needle carriage 113 interrupts optical circuit 325 in right end block 121 when carriage 113 is fully to the right, i.e., when the tip of needle 109 is inside specimen tube 3.

Optical circuit 325 is a type TIL 138 circuit and is connected to circuit 323 in the same manner as circuits 255, etc. When needle 109 is in specimen tube 3, or equivalently when right bolt 249 is in optical circuit 325, the output of buffer 323 is Low, otherwise it is High.

Normally, penetrating means 13 is in its fully retracted position, so the output of buffer 323 is High and the output of NAND gate G25 therefore is Low. This Low is supplied to a NAND gate G26 which supplies its High output to a NAND gate G27 which constitutes interlocking means for preventing movement of needle 109 toward feed screw S1 unless bore 143 is aligned with needle 109. When door 17 is closed and both positioning holes are aligned with their respective optical circuits, the other input to gate G27 is also High, so its output is Low. This Low is supplied to an inverter 327 which supplies a High output through a 1K resistor R6 to the base of a transistor Q3. The emitter of transistor Q3 is connected to ground and the collector is connected through a 130-ohm resistor R7 to pin 4 of a General Electric Type CR120SR105D solid-state relay, designated as SSR.

Pin 3 of relay SSR is connected to a 5-volt voltage source V6. Pin 1 is connected to a 110-volt a.c. voltage source. Pin 2 is connected by a line SL15 to a 50-rpm motor sold by Dayton Brake Gear Co., under stock number 3M258, designated as M3. When the output of inverter 327 is High, transistor Q3 conducts, which causes solid-state relay SSR to activate motor M3. Motor M3 powers chain-and-sprocket drive 129, thereby moving penetrating means 13 from the fully retracted position to the fully extended position. This causes needle 109 to be inserted into the lower end of specimen tube 3. Motor M3 is thus part of the means for reciprocating needle 109 between its retracted and extended positions.

When penetrating means 13 reaches its fully extended position, the output of buffer 323, which constitutes means for detecting when needle 109 is in its extended position, goes Low, causing the output of gate G25 and one input of gate G26 to go High. The other input of gate G26 is connected to a NAND gate G28, one of whose inputs is the Q output of latch 245. This output is Low, so the output of gate G28 is High. The output of gate G26 goes Low, therefore, which stops conduction of transistor Q3 and thereby stops motor M3, causing needle 109 to dwell inside tube 3.

The Low output of buffer 323 is also supplied to the clear input of a binary counter 329, thereby enabling it, which counter constitutes means for maintaining needle 109 in the fully extended position for a predetermined interval of time. The up clock input of counter 329 is supplied via a line L11 with 2 Hz clock pulses from a clock 331. Counter 329 is programmed to supply a Low carry output at the end of 8 seconds. During these 8 seconds, the sample is aspirated from specimen tube 3. Of course this sampling time can be shortened or lengthened as desired. The Low carry output is supplied, via a diode D7, to the set input of latch 245, causing its Q output to go High. The output of gate G28 goes Low as a result, which eventuates in motor M3 being reactivated and moving penetrating means 13 to its fully retracted position. At that time the output of buffer 255 goes Low, making the output of gate G28 High, which results in motor M3 stopping penetrating means 13 in its fully retracted position.

During aspiration of the sample, the Low output of buffer circuit 323 is also supplied, via a line L12 and a diode D8, to an inverter 333 in feed section 177. Inverter 333 supplies its resulting High output to NAND gate G8, the other input of which is supplied on line L4 from tilt section 173 and is also High. The output of gate G8 is therefore Low. This Low resets latch 247 so that its $\overline{Q}$ output is High and its Q output is Low. This results in latch 221 in tilt section 173 being set so that its $\overline{Q}$ output is Low. This in turn causes the input of gate G5 and input 205 of gate G3 to be High, in preparation for further operation of the apparatus.

Once penetrating means 13 is fully retracted, the output of buffer 255 goes Low, making the output of inverter 257, and thereby the non-clock pulse input of gate G12, High. As a result, clock pulses again pass from master run control section 167 to screw rotation control section 181.

These clock pulses causes screw S2 to rotate down. Only screw S2 rotates; screw S1 is prevented from rotating because both inputs of gate G15 are High. The direction of rotation is down because the Low Q output of feed section latch 247 has been supplied, via a line L13 and a diode D9, to gate G19, causing its output to be High. This output, as described above, is supplied to gate G11, making its output Low, which prevents upward rotation.

Screw S2 rotates down for 160 steps while screw S1 is stationary. At this point specimen tubes 3 are again level and accumulator 265 supplies High outputs to a NAND gate G29 causing all of its inputs to be High, and its output to be Low. This Low output is supplied, via a diode D10, to gate G15, enabling rotation of screw S1. Screws S1 and S2 now rotate down together for an additional 400 steps (1 full revolution) dumping the sampled specimen tube 3 onto collars 146 and 147.

At the conclusion of this full revolution, the output of a NAND gate G30, connected to the appropriate outputs of accumulator 265, goes Low. This sets the Q output of feed section latch 247 High and the $\overline{Q}$ output Low. It also causes the output of "up" gate G11 to be High and that of "down" gate G10 to be Low, i.e., further downward rotation of screws S1 and S2 is prevented. At this point the positioning hole of screw S1 is again in optical circuit 273, so further movement of screw S1 is inhibited. Screw S2 rotates up, tilting those specimen tubes 3 remaining between the screws, until its positioning hole aligns with optical circuit 279. Screw S2 then stops rotating because of the resulting Low output of gate G17, and screw S1 starts rotating up for the same reason. If a tube 3 is present at sampling station 11, screw S1 will go through another mixing cycle, i.e., rotate up and down 16 times. During this second mixing cycle, the first tube 3 sampled rotates on collars 146 and 147 permitting identification of the tube to be made. The second tube 3 is sampled just the same as the first tube and is then dumped onto collars 146 and 147. As screws S1 and S2 rotate one full revolution to dump the second tube onto the collars, notch 153 rotates under first specimen tube 3 and it falls stoppered end first into drawer 155.

This mixing-sampling-dumping cycle is repeated until no specimen tube 3 is sensed at sampling station 11, at which time the output of buffer 313 is High. The output of inverter 321 is therefore Low and the output of gate G6 is High, which ensures that the $\overline{Q}$ output of latch 245 is Low. Since penetrating means 13 is in its fully retracted position, gates G25 and G28 both have at least one Low input and High outputs, which causes the output of gate G26 to be Low. This ensures that motor M3, which would normally be actuated at this point in the cycle, is not actuated and that penetrating means 13 does not move (futilely) to its extended position. That is, tube-sensing section 169 and penetrating means control section 175 constitute means responsive to the presence of closed container 3 at sampling station 11 for retaining needle 109 in retracted position unless specimen tube 3 is present at sampling station 11.

Tube-sensing section 169 also constitutes means responsive to the presence of closed container 3 at sampling station 11 for deactivating the apparatus unless a closed container 3 is sensed at sampling station 11 at a predetermined time in the sampling cycle. The High output of buffer circuit 313 is supplied to gate G7 causing its output to go Low. This Low output is supplied by a line L14 to feed section 177 where it resets latch 247, causing the Q output of latch 247 to be Low. Screws S1 and S2 thereupon go through the feed cycle, causing any tube 3 on collars 146 and 147 to fall into drawer 155. Just as is the case when tube 3 is present at sampling station 11, screw S2 rotates up until its positioning hole is aligned in optical circuit 279, at which time it stops and screw S1 starts rotating up. The absence of specimen tube 3 at sampling station 11, however, prevents screw S1 from completing another mixing cycle. Because no tube 3 is present, the Q output of tube-sensing latch 219 is set High. This High output is supplied via line L9 to input 307 of gate G23 in load section 171. Once screw S1 completes 160 steps up, all the inputs of gate G23 are High, causing its output to be Low and causing a High signal to be supplied via a line L15 to the clear input of counter 189. This again causes output 191 of counter 189 to go Low, which prevents further clock pulses from passing from master run control 167 to screw rotation control section 181. Screw S1 therefore stops rotating. The Low output 191 of counter 189 is also supplied to Gate G2 causing its output to be High, which results in "Run" light 197 being turned off. Sampler 1 is now in the loading position. Having sampled the previous series of specimen tubes 3, it is now ready to accept a new batch of tubes.

Door 17 is now opened and a new series of specimen tubes 3 is inserted between the threads of screws S1 and S2. The entire process is then repeated by pushing "Run" button 199. It can be seen that sampler 1 mixes and samples a large number of specimen tubes 3 very efficiently with a minimum of human effort. The major task the operator must perform is loading each series of tubes into the sampler. Since rubber stopper 7 reseals specimen tubes 3 after needle 109 has been withdrawn, the operator need never be exposed to or handle the blood or blood serum itself. And the sampled tubes 3 are removed from sampler 1 simply by opening drawer 155 and taking them out en masse.

The operator can change the functioning of sampler 1, however. Once specimen tubes 3 have been loaded and door 17 has been closed, or at any time during the mixing cycle, the operator can cause the specimen tube near sampling station 11 to be sampled immediately by pressing a momentary-contact push button "Stat" switch, designated by the reference numeral 335. The face of Stat switch 335 is shown on FIG. 15D; the switch itself on FIG. 15A. Pressing Stat switch 335 connects a five-volt voltage source V4 through a 1K resistor R8 to the base of an n-p-n transistor Q4. The emitter of transistor Q4 is connected to ground and its collector is connected through a 10K resistor R9 to voltage source V4. Transistor Q4 conducts, causing a Low to appear on its collector. This Low is supplied to the set input of a latch 337, causing its Q output to be High. The High Q output is supplied through a 1K resistor R10 to the base of a n-p-n transistor Q5, the collector of which is connected to voltage source V4 by way of a Stat switch indicator lamp 335a and the emitter of which is connected to ground. Transistor Q5 conducts, causing lamp 335a to light.

The Low on the collector of transistor Q4 is also supplied to the reset input of tube sensing latch 219, the load input of counter 189, and the reset input of tilt section latch 211. As a result the Q output of tube sensing latch 219 goes Low. This Q output is supplied via line L9 to input 307 of gate G23 in load section 171, causing its output to be High. This High output is inverted by inverter 309 and the resulting Low is supplied to the clear input of counter 189, thereby enabling it. The Low supplied to the load input of counter 189, since the clear input is Low, causes output 191 to go High, which supplied to input 201 of master run gate G3. Unless tube 3 is already in position to be sampled, the output of gate G3 is now clock pulses, which are supplied to screw rotation control section 181.

The Low supplied to the reset input of tilt latch 221 initiates a homing function of screw S1. If screw S1 is rotating up when Stat button 335 is pressed, the output of up gate G11 will be High. This High output is supplied to gate G9 in tilt section 173. The other input of Gate G9 is supplied from the $\bar{Q}$ output of tilt latch 221 and is also High. The resulting Low output of gate G9 is supplied to "down" gate G10, causing its output to be High, which in turn causes the output of "up" gate G11 to go Low. This stops further upward rotation of screw S1 and starts it rotating down. Of course, if screw S1 is already rotating down, the $\bar{Q}$ output of tilt latch 221 does not change the direction of rotation.

The High $\bar{Q}$ output of tilt latch 221 is also supplied to gate G5. As soon as screw S1 moves specimen tube 3 to sampling station 11, the output of gate G5 goes Low. This Low output is supplied to master run gate G3, stopping the flow of clock pulses to screw rotation control section 181 and thereby stopping rotation of screw S1. Sampling then proceeds as described above. Of course, imposing an external Low, indicated by reference numeral 336, on the reset input of tilt latch 221 while mixing is occurring is functionally equivalent to pressing Stat button 335. After sampling, sampler 1 feeds tube 3 down to collars 146 and 147 as before. After 160 steps in the feed mode, the output of gate G29 in screw rotation control section 181 goes Low. This Low output is supplied via a line L16 to the reset input of Stat latch 337, which turns off Stat indicator lamp 335a.

The Stat feature of sampler 1 is particularly useful where a single premixed specimen tube is to be sampled. The operator places the ends of such a tube between the threads of screws S1 and S2, closes door 17 and presses Stat button 335. The tube is immediately tilted and sampled, without sampler 1 going through its regular mixing cycle. To ensure that the single tube to be sampled is placed at the right position along predetermined path 9, screws S1 and S2 are provided with loading dots (not shown) which indicate the correct place along path 9 to load the single tube.

It is desirable in the case of blood serum specimens to sample a series of specimen tubes 3 without going through the mixing cycle. This is because of the thixotropic barrier layer in serum separator tubes which could be broken down by excessive movement of the tubes. The operator eliminates the mixing cycle of sampler 1 easily and simply by switching mix control switch 217 off, which actuates mix control section 163.

Mix control section 163 includes NAND gate G4 and two additional NAND gates, designated by the reference characters G31 and G32. The output of gate G31 is connected to the chip select input of PROM 287 via a line L17 and switch 217. When the output of gate G31 is Low, PROM 287 is enabled and screw S1 can be rotated. When the output of gate G31 is High, PROM 287 is disabled, preventing energization of stepper motor M1 and preventing rotation of screw S1.

One input to gate G4 is the momentary Low on line L1 which occurs when "on" button 183 is pushed. This causes the output of gate G4 to be High. This High output is supplied to gate G31. The other input of gate G31 is the output of gate G32. This is also High causing the output of gate G31 to be Low and PROM 287 to be enabled. The Low output of gate G31 is also supplied back to gate G4, completing a latch 339 consisting of gates G4 and G31.

PROM 287 remains enabled as screw S1 rotates up to the loading position, as previously described. After screw S1 has rotated up 160 steps, all inputs to gate G32 are High which causes its output to go Low. This Low output is supplied to gate G31 causing its output to be High and resetting latch 339. This disables PROM 287, preventing further rotation of screw S1. Specimen tubes 3 containing blood serum are then loaded into sampler 1 and Run button 199 is pressed. As described above, this causes clock pulses to be supplied from master run gate G3 to screw rotation control section 181. Screw S1 does not move, however, since its PROM has been disabled. The only effect of the clock pulses on section 181 is to cause accumulator 265 to count and supply inputs to gate G24.

The output of gate G24 is Low whenever the outputs of accumulator 265 corresponding to counts of 256 and 64 are both High. The output of gate G24 is supplied to cycle counter 179 which counts the Low-to-High transitions in the output of gate G24. After 16 of these transitions, the carry output of cycle counter 179 goes Low, resetting tilt latch 221. Until this Low carry output occurs, specimen tubes 3 remain stationary between screws S1 and S2. When the Q output of tilt latch 221 goes Low, it is supplied via a line L18 to gate G4 causing its output to be High, which in turn causes the output of gate G31 to be Low. PROM 287 is thereby enabled and screw S1 rotates down to move a specimen tube to the tilted position at sampling station 11. Sampling and feeding of specimen tubes 3 then occurs just as in the mixing mode. Specifically, in the feed mode, screw rotation control section 181 constitutes means for energizing motors M1 and M2 so that screws S1 and S2 rotate at the same rate, feeding the sampled tube 3 onto collars 146 and 147 and feeding the remaining tubes 3 sequentially to sampling station 11. Similarly after feeding, screw S2 rotates up until its positioning hole is aligned with optical circuit 279, where it stops, and screw S1 then begins rotating up. But after rotating up 160 steps, screw S1 is again stopped since mix control section 163 disables PROM 287. Specimen tubes 3 remain horizontal until cycle counter 179 again supplies its Low carry output to tilt section 173, at which time tilting and sampling of the next tube occurs. This process continues until all the blood serum tubes have been sampled.

The operation of sampler 1 is thus identical in the nonmixing mode to its operation in the mixing mode except for the absence of the mixing up-and-down rotation of screw S1 in the former mode. Simply by flipping a switch, the operator chooses the mode of operation desired. As a convenience, a line 341 can be inscribed on scale 39 to separate the pictures of blood specimen tubes from the pictures of the serum separator tubes, which are typically longer. If, in setting the screw spacing, pointer 37 indicates that a serum separator tube is being inserted, the operator will be reminded to turn off mixing switch 217.

Sampler 1 has several other safety features, foremost of which is a door interlock system, indicated generally at 343, which constitutes means for preventing movement of screws S1 and S2 and penetrating means 13 whenever door 17 is open. Door interlock system 343 consists of a microswitch 345 having a contact 345a connected to voltage source V2 through resistor R2, a contact 345b connected to ground and an actuator 345c which engages door 17 when it is closed. The front exterior of switch 345 is shown in FIG. 15D. Contacts 345a and 345b, along with the electrical connections are shown in FIG. 15A. If door 17 is closed, contacts 345a and 345b are not connected and sampler 1 functions normally. If door 17 is open, however, actuator 345c closes switch 345, grounding voltage source V2. If Run button 199 is pushed while door 17 is open, Run light 197 will flash on and off at a frequency of 2 Hz. The Low resulting from the grounding of voltage source V2 is supplied to input 203 of master run gate G3, stopping the flow of clock pulses to screw rotation control section 181, thereby inhibiting further rotation of either screw. The Low is also supplied to gate G27 in penetrating means control section 175, causing its output to be High, which ensures that motor M3 is not activated. Penetrating means 13 is, therefore, immobilized when door 17 is open. As a result of this interlock system, the operator can at any time, with complete safety, open door 17 without danger of becoming entangled in any moving parts.

The Low resulting from door 17 being open is also supplied via a line L19 to an inverter 347, which supplies its High output to the clear input of cycle counter 179. Thus, if door 17 is opened while mixing is occurring, sampler 1 will start mixing from the beginning once the door is closed. This feature ensures that no matter how long door 17 is open the samples will be thoroughly mixed.

Door interlock system 343 is also used to advantage when, for some reason, tube 3 has not fallen off collars 146 and 147 into drawer 155 during the feed cycle. Collar 147 has mounted thereon a second pin, designated by the reference numeral 349, which rotates counterclockwise as seen in FIG. 14 with screw S2 during the feed cycle. If the tube 3 resting on collars 146 and 147 does not fall into drawer 155 when notch 153 rotates under it, pin 349 will push tube 3 forwardly against door 17 opening the interlock and stopping rotation of screws S1 and S2 before a second tube 3 is dumped on top of the first tube 3. The operator can then easily remove the stuck tube manually.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for obtaining samples from specimens of blood or the like contained in a series of closed containers, which specimens include a plurality of particles such as cells, comprising:
   means for moving the closed containers along a predetermined path to a sampling station and for imparting motion to the closed containers while they are moved along the path to obtain a substantially uniform distribution of the particles contained therein; and
   means for penetrating the closed containers when they reach the sampling station to withdraw specimen samples from said containers.

2. Apparatus as set forth in claim 1 wherein the moving means comprises substantially parallel first and second feed screws spaced from each other in order to engage the closed containers at longitudinally spaced positions, the feed screws defining the predetermined path.

3. Apparatus as set forth in claim 2 further including means extending along said path for enclosing the path.

4. Apparatus as set forth in claim 3 wherein the enclosing means includes a door and further including means for preventing movement of the feed screws when the door is open.

5. Apparatus as set forth in claim 2 further including a receptacle positioned so that the closed containers fall from the feed screws into the receptacle after sampling.

6. Apparatus as set forth in claim 5 further including means for interrupting the fall of each closed container in order to allow identification of said container.

7. Apparatus as set forth in claim 2 further including means for retaining the closed containers in engagement with the feed screws as they move along the predetermined path.

8. Apparatus as set forth in claim 7 wherein the retaining means includes at least one support positioned intermediate the feed screws.

9. Apparatus as set forth in claim 2 further including means for adjusting the spacing between the feed screws so that the feed screws may accommodate various sized closed containers.

10. Apparatus as set forth in claim 9 wherein the position of the first feed screw is fixed and the adjusting means includes means for moving the second feed screw relative to the first feed screw.

11. Apparatus as set forth in claim 10 wherein the adjusting means includes means for supporting the second feed screw, at least one channel adapted for movement of the supporting means therein, and means for moving the supporting means in the channel to change the spacing between the feed screws.

12. Apparatus as set forth in claim 2 wherein the feed screws have crests and roots and the spacing between the first and second screws is such that the opposite ends of the closed containers rest between adjacent facing portions of the walls of the respective screws.

13. Apparatus as set forth in claim 12 wherein the spacing between the roots of the first and second screws is not less than the length of the closed container and the spacing between the crests of the first and second screws is not greater than the length of the closed container.

14. Apparatus as set forth in claim 12 wherein the pitch of each feed screw is substantially constant throughout its length and the pitches of the feed screws are substantially identical.

15. Apparatus as set forth in claim 12 wherein the root of the first feed screw is wider than the root of the second feed screw.

16. Apparatus as set forth in claim 12 wherein the feed screws are vertical and the closed containers are moved downwardly on the predetermined path to the sampling station.

17. Apparatus as set forth in claim 16 further including first and second collars fixed to the respective bottoms of the first and second feed screws.

18. Apparatus as set forth in claim 17 further including means for retaining the closed containers on the collars.

19. Apparatus as set forth in claim 12 wherein a wall of at least one of the screws is adapted to frictionally engage one end of the closed containers to rotate them about their longitudinal axes thereby to mix the particles in the specimens.

20. Apparatus as set forth in claim 12 wherein the crests of the feed screws are pitched in opposite directions and the feed screws are rotated in opposite directions to move the closed containers along the predetermined path.

21. Apparatus as set forth in claim 2 wherein one end of the container at the sampling station is puncturable and the penetrating means includes a needle insertable into said puncturable end of said container, the needle being hollow and having an opening therein through which a specimen sample may be admitted into the needle.

22. Apparatus as set forth in claim 21 wherein the penetrating means includes means for reciprocating the needle between a retracted position and an extended position, the needle penetrating the puncturable end of the closed container at the sampling station as it moves toward its extended position.

23. Apparatus as set forth in claim 22 further including means for tilting the closed container at the sampling station so that one end of said container is lower than the other end.

24. Apparatus as set forth in claim 23 wherein the end of the closed container at the sampling station tilted lower than the other end by the tilting means is the puncturable end whereby the needle may be inserted into the lower end of said container.

25. Apparatus as set forth in claim 22 wherein the reciprocating means includes means for detecting when the needle is in the extended position and means for maintaining the needle in the extended position for a predetermined interval of time.

26. Apparatus as set forth in claim 22 wherein the reciprocating means includes means responsive to the presence of a closed container at the sampling station for retaining the needle in the retracted position unless a closed container is present at the sampling station.

27. Apparatus as set forth in claim 22 wherein the reciprocating means includes a track, a carriage for the needle, the carriage being adapted for movement along the track to move the needle between its retracted and its extended positions, and carriage drive means for moving the carriage over the track.

28. Apparatus as set forth in claim 27 further including a waste chamber with which the needle communicates when at its retracted position so that the needle may be cleaned and any waste material collected in the chamber.

29. Apparatus as set forth in claim 27 wherein the penetrating means further includes a rod slidably mounted inside the needle, the outside diameter of the rod being slightly smaller than the inside diameter of the needle.

30. Apparatus as set forth in claim 29 further including a second carriage on which said rod is mounted, said second carriage being slidably mounted on said track, the position of the rod inside the needle being determined by the relative positions of the first and second carriages, the second carriage being movable to a first position relative to the first carriage in which the rod blocks the opening in the needle and to a second position in which the opening in the needle is unblocked, the carriage drive means further including means for moving both carriages along the track with the second carriage in its first position relative to the first carriage as the needle penetrates the puncturable end of the closed container dwelling at the sampling station and for moving the second carriage to its second position relative to the first carriage after said puncturable end is penetrated thereby to unblock the opening in the needle in order to admit a sample of the specimen into said needle.

31. Apparatus as set forth in claim 30 further including a waste chamber with which the needle communicates when at its retracted position, and wherein the carriage drive means further includes means for moving the second carriage to its second position relative to the first carriage when the needle is in its retracted position, whereby the needle may be cleaned and any waste material collected in said chamber.

32. Apparatus as set forth in claim 31 wherein the rod has a longitudinal bore therethrough whereby a sample admitted through the opening in the needle may be drawn through the rod.

33. Apparatus as set forth in claim 32 wherein one of the feed screws has a bore extending diametrically therethrough at the sampling station, and including means for aligning the bore with the needle when a closed container is at the sampling station thereby permitting movement of the needle through said one feed screw in order to penetrate the puncturable end of the container at the sampling station, and further including interlocking means for preventing movement of the needle toward said one feed screw unless the bore is aligned with the needle.

34. Apparatus as set forth in claim 2 further including a motor for each feed screw adapted to rotate its associated feed screw independently.

35. Apparatus as set forth in claim 34 further including means for controlling energization of each motor.

36. Apparatus as set forth in claim 35 wherein the control means includes means for rotating one of the feed screws at a rate which differs from the rate of rotation of the other feed screw in order to move one end of the closed containers relative to the other end thereby to mix the particles in the specimens.

37. Apparatus as set forth in claim 35 wherein the control means includes means for changing the direction of rotation of at least one of the feed screws in order to move one end of the closed containers relative to the other end thereby to mix the particles in the specimens.

38. Apparatus as set forth in claim 37 wherein each feed screw motor is a stepper motor and the control means further includes means for selectively rotating one feed screw a predetermined number of steps clockwise and counter-clockwise with respect to its longitudinal axis thereby rotating said one feed screw through a partial revolution while not simultaneously rotating the other feed screw a like number of steps.

39. Apparatus as set forth in claim 38 wherein the control means further includes means for stopping the selective rotation of the one feed screw after a predetermined number of partial revolutions.

40. Apparatus as set forth in claim 37 wherein the control means further includes means for rotating the feed screws to a loading position and maintaining them in the loading position so that the closed containers can be loaded into the apparatus.

41. Apparatus as set forth in claim 35 wherein the control means includes means for stopping the motors when one of the closed containers reaches the sampling station in order to cause said container to dwell at the sampling station.

42. Apparatus for obtaining samples from specimens of blood or the like contained in a series of closed containers, which specimens include a plurality of particles such as cells, comprising:
    means for moving the closed containers along a predetermined path to a sampling station;
    means for penetrating the closed containers when they reach the sampling station to withdraw specimen samples from said containers; and
    control means for positioning one end of the closed container at the sampling station lower than the other end.

43. Apparatus as set forth in claim 42 wherein the control means includes means for tilting the closed container at the sampling station so that the penetrating means penetrates the lower end of said container.

44. Apparatus as set forth in claim 43 wherein the moving means comprises substantially parallel first and second feed screws spaced from each other in order to engage the closed containers at longitudinally spaced positions, the feed screws defining the predetermined path and having helical crests and roots.

45. Apparatus as set forth in claim 44 further including a motor for each feed screw adapted to rotate its associated feed screw independently.

46. Apparatus as set forth in claim 45 wherein the control means includes means for controlling energization of each motor.

47. Apparatus as set forth in claim 46 wherein the pitch of the feed screws is substantially identical and wherein the control means includes means for energizing the feed screw motors so that the feed screws rotate at the same rate thereby feeding the closed containers sequentially to the sampling station.

48. Apparatus as set forth in claim 47 wherein the control means includes means for stopping the motors when one of the closed containers reaches the sampling station in order to cause said container to dwell at the sampling station.

49. Apparatus as set forth in claim 44 wherein the feed screws are vertical and the closed containers are moved downwardly on the predetermined path to the sampling station.

50. Apparatus as set forth in claim 49 wherein the feed screws are pitched in opposite directions and further including supporting means on one side of the feed screws for retaining the closed containers in engagement with the feed screws as they move along the predetermined path.

51. Apparatus as set forth in claim 49 further including a door positioned on the opposite side of the feed screws from the supporting means.

52. Apparatus as set forth in claim 51 wherein the directions of pitch of the feed screws are such that the closed containers will remain resting between said screws when the door is open and the screws are not rotating.

53. Apparatus as set forth in claim 42 including means responsive to the presence of a closed container at the sampling station for deactivating the apparatus unless a closed container is sensed at the sampling station at a predetermined time in a sampling cycle of the apparatus.

* * * * *